(12) United States Patent
Narayan et al.

(10) Patent No.: US 11,495,369 B2
(45) Date of Patent: Nov. 8, 2022

(54) LASER STRUCTURED, COATED ELECTRICAL CONDUCTOR AND METHOD FOR PRODUCING SAME

(71) Applicants: Heraeus Deutschland GmbH & Co. KG, Hanau (DE); Heraeus Medical Components LLC, St. Paul, MN (US)

(72) Inventors: Suman Narayan, Hanau (DE); Leonard Stoica, Hanau (DE); Andreas Liess, Hanau (DE); Benjamin Pobiel, St. Paul, MN (US)

(73) Assignees: Heraeus Deutschland GmbH & Co. KG, Hanau (DE); Heraeus Medical Components LLC, St. Paul, MN (US)

( * ) Notice: Subject to any disclaimer, the term of this patent is extended or adjusted under 35 U.S.C. 154(b) by 90 days.

(21) Appl. No.: 17/213,082

(22) Filed: Mar. 25, 2021

(65) Prior Publication Data

US 2022/0310282 A1   Sep. 29, 2022

(51) Int. Cl.
*H01B 5/14*     (2006.01)
*H01B 13/00*    (2006.01)
*H01B 1/12*     (2006.01)
*A61N 1/05*     (2006.01)

(52) U.S. Cl.
CPC ............. *H01B 5/14* (2013.01); *H01B 1/124* (2013.01); *H01B 13/003* (2013.01); *A61N 1/05* (2013.01)

(58) Field of Classification Search
CPC ........ H01B 1/124; H01B 5/14; H01B 13/003; A61N 1/05
USPC .......................................................... 174/36
See application file for complete search history.

(56) References Cited

U.S. PATENT DOCUMENTS

| | | | | |
|---|---|---|---|---|
| 5,318,572 A | * | 6/1994 | Helland | A61N 1/0565 607/121 |
| 5,571,158 A | * | 11/1996 | Bolz | A61N 1/05 607/121 |
| 6,799,076 B2 | * | 9/2004 | Gelb | A61N 1/0565 607/121 |
| 9,117,680 B2 | | 8/2015 | Fisk | |
| 10,219,715 B2 | | 3/2019 | Fisk | |
| 10,791,945 B2 | | 10/2020 | Fisk | |

(Continued)

FOREIGN PATENT DOCUMENTS

| EP | 2886155 B1 | 1/2018 |
|---|---|---|
| EP | 3500419 B1 | 5/2020 |
| WO | 2014/124231 | 8/2014 |

*Primary Examiner* — William H. Mayo, III
(74) *Attorney, Agent, or Firm* — Dicke, Billig & Czaja, PLLC

(57) ABSTRACT

An electrical conductor has a first layer, wherein the first layer is electrically conducting, and has micro protrusions, macro protrusions, wherein the micro protrusions are arranged on the macro protrusions, a first set of depressions, wherein the first set of depressions comprises at least two longitudinal depressions; the macro protrusions and the at least two longitudinal depressions are arranged in an alternating pattern, at least one coating layer, wherein the at least one coating layer comprises an electrically conducting polymer, touches the first layer, at least partially covers the first layer; wherein at least 50% of the macro protrusions have a width, measured along a first direction in the range of 2.0 mm to 40.0 mm and at least 50% of the micro protrusions have a width, measured along the first direction, in the range of 0.001 mm to 1.000 mm.

18 Claims, 12 Drawing Sheets

(56) References Cited

U.S. PATENT DOCUMENTS

| | | | |
|---|---|---|---|
| 2008/0299289 A1* | 12/2008 | Fisk | C23C 14/541 |
| | | | 607/116 |
| 2011/0160821 A1* | 6/2011 | Jackson | A61N 1/056 |
| | | | 607/116 |
| 2013/0296678 A1 | 11/2013 | Larsen et al. | |
| 2016/0059353 A1 | 3/2016 | Dodds | |
| 2019/0159833 A1 | 5/2019 | Sutermeister et al. | |
| 2019/0283176 A1 | 9/2019 | He et al. | |

* cited by examiner

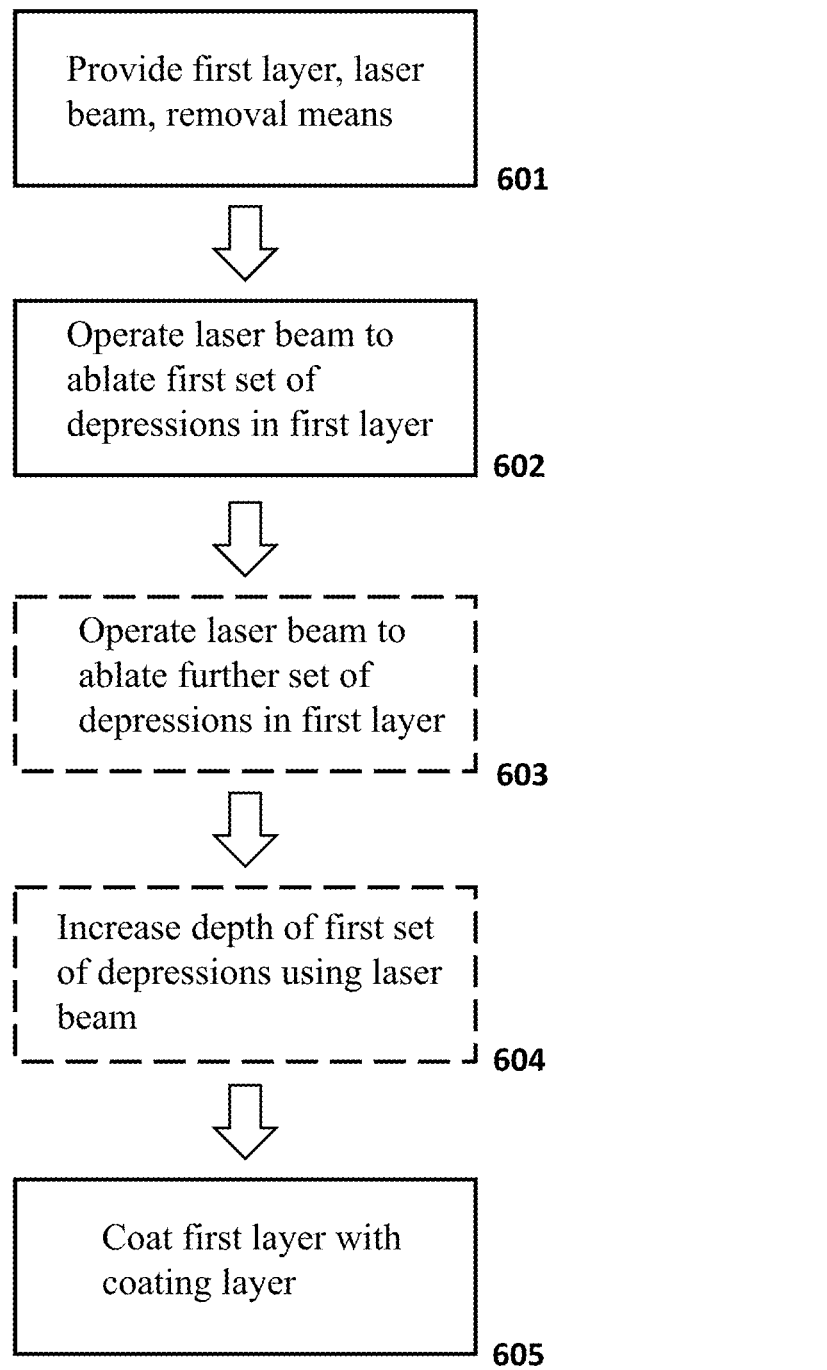

LASER STRUCTURED, COATED ELECTRICAL CONDUCTOR AND METHOD FOR PRODUCING SAME

FIELD OF THE INVENTION

The invention relates to an electrical conductor comprising an electrically conductive first layer and an electrically conductive coating layer. The invention also relates to a method for producing the electrical conductor. The invention further relates to a use of the electrical conductor.

BACKGROUND OF THE INVENTION

Medical devices, and especially active implantable medical devices, generally comprise electrodes to electrically stimulate, or to measure electrical signals produced by, body tissue. Examples of body tissue include muscles and nerves. These electrodes also comprise electrical conductors.

For the aforementioned electrical conductors, there are a number of very important requirements. A first requirement is that the electrical conductor should have a very low impedance, especially at the lower frequencies in the range of 0.1 Hz to 100 Hz. This low-frequency range is of particular importance to the above-mentioned medical devices. A very low impedance is essential for ensuring a good signal-to-noise ratio. Another requirement is that the electrical conductor should have a high charge storage capacity. A further requirement is that the electrical conductor should have a long-term stability. This means that the electrical properties, e.g., the impedance and charge storage capacity, of the electrical conductor should not change with time. This is essential for medical devices used for stimulation, as the electrical signal should not vary with time. This long-term stability is also important for medical devices used for mapping and sensing, as this influences the measurement accuracy of the medical device.

Electrical conductors very often comprise a first layer, but not a coating layer. A lack of a coating layer has the disadvantage that these electrical conductors have a very high electrical impedance, especially at the lower frequencies in the range of 0.1 Hz to 100 Hz. Uncoated electrical conductors also have a low charge storage capacity, as well as a low signal to noise ratio.

The electrical impedance can be reduced by low impedance coatings such as TiN- or fractal Ir-coatings on the surface of the first layer. However, this has the disadvantage that the adhesion of the coating layer to the first layer is always limited. Over time, parts of the coatings can detach from the first layer and can be released to the surrounding of the electrical conductor. This can be highly problematic as detached parts of the coating layer can cause inflammation in adjacent body tissue, and therefore can have negative consequences for the health of a patient. Furthermore, the impedance of coatings such as TiN- or fractal Ir-coatings is very often still too high, especially in the 0.1 Hz to 100 Hz range. Furthermore, these electrical conductors also have a low charge storage capacity, as well as poor long-term stability.

It is known from, e.g., U.S. Pat. No. 10,219,715 B2, that the electrical properties of the electrical conductor, e.g., the impedance and the charge storage capacity, can be improved by using laser ablation to structure the first layer. However, even in this case the impedance remains too high, especially in the 0.1 Hz to 100 Hz range, and the charge storage capacity too low.

The first layer can alternatively be coated with an electrically conductive polymer to improve the aforementioned electrical properties, as disclosed in e.g., US 2019/0159833 A1. However, adhesion of the electrically conductive polymer to the first layer is difficult to achieve, especially if the electrical conductor is subjected to mechanical stresses and forces. As a result, it very often occurs that sections of the electrically conductive polymer becomes detached from the first layer. Adhesion of a polymer coating can be improved when laser structuring the first layer, as disclosed in e.g., EP 3500419 B1. However, even in this case adhesion remains problematic. This lack of adhesion not only negatively influences the patient, but also the electrical properties and long-term stability of the electrical conductor.

OBJECTS OF THE INVENTION

An object of the present invention is to at least partially overcome at least one of the disadvantages encountered in the state of the art.

It is a further object of the invention to provide an electrical conductor that has a reduced impedance.

It is a further object of the invention to provide an electrical conductor that has an increased charge storage capacity.

It is a further object of the invention to provide an electrical conductor that has an increased robustness to damage resulting from mechanical forces and stresses. Examples of damage resulting from mechanical forces is the damage that results when, e.g., the electrical conductor is inserted or withdrawn from the body of a mammal, or handled by an operator.

It is a further object of the invention to provide an electrical conductor, comprising a first layer and at least one coating layer, that has an increased adhesion of the at least one coating layer to the first layer.

It is a further object of the invention to provide an electrical conductor that has an improved long-term stability.

It is a further object of the invention to provide an electrical conductor that, when used to take measurements, increases the accuracy of the measurements.

It is a further object of the invention to provide a method for producing an electrical conductor that at least partially solves at least one of the above objects, e.g., a lower electrical impedance, a higher charge storage capacity, or improved long-term stability.

It is a further object of the invention to provide a method for producing an electrical conductor that requires less cleaning of the first layer during the production of the electrical conductor.

It is a further object of the invention to provide a measuring device, comprising at least one electrical conductor, that has an increased measurement accuracy. An example of a measuring device is a device used for heart catheter mapping.

It is a further object of the invention to provide a stimulation device, comprising at least one electrical conductor, that has improved stability when providing an electrical signal. An improved stability is obtained when the variation in the electrical signal, over time, is reduced. An example of a stimulation device is a cardiac defibrillator.

SUMMARY OF THE INVENTION

A contribution to at least partially fulfilling at least one of the above-mentioned objects is made by any of the variants of the invention.

A first (1$^{st}$) variant of the invention is an electrical conductor comprising
a. a first layer, wherein the first layer
   i. is electrically conducting, and
   ii. comprises
      A. micro protrusions,
      B. macro protrusions, wherein the micro protrusions are arranged on the macro protrusions,
      C. a first set of depressions, wherein the first set of depressions comprises at least two longitudinal depressions;
      D. the macro protrusions and the at least two longitudinal depressions are arranged in an alternating pattern,
b. at least one coating layer, wherein the at least one coating layer
   i. comprises an electrically conducting polymer,
   ii. touches the first layer,
   iii. at least partially covers the first layer;
wherein
   I. at least 50%, preferably at least 70%, and more preferably at least 85% of the macro protrusions have a width, measured along a first direction, in the range of 2.0 μm to 40.0 μm, preferably in the range of 5.0 μm to 25.0 μm, more preferably in the range of 7.0 μm to 20.0 μm, and further preferably in the range of 10.0 μm to 15.0 μm;
   II. at least 50%, preferably at least 70%, and more preferably at least 85% of the micro protrusions have a width, measured along the first direction, in the range of 0.001 μm to 1.000 μm, preferably in the range of 0.001 μm to 0.700 μm, more preferably in the range of 0.001 μm to 0.500 μm, further preferably in the range of 0.001 μm to 0.300 μm, even further preferably in the range of 0.001 μm to 0.100 μm, particularly preferably in the range of 0.001 μm to 0.080 μm, and more particularly preferably in the range of 0.001 μm to 0.050 μm.

In an aspect of the 1$^{st}$ variant, it is preferred that at least 50%, more preferably at least 70%, and further preferably at least 85% of the longitudinal depressions in the first set of depressions are arranged perpendicular to the first direction.

In a preferred variant of the electrical conductor, the first layer further comprises a further set of depressions, wherein the further set of depressions comprises at least two longitudinal depressions. This preferred variant is a 2$^{nd}$ variant of the invention, that preferably depends on the 1st variant of the invention. In an aspect of the 2$^{nd}$ variant, it is preferred that at least 50%, more preferably at least 70%, and further preferably at least 85% of the longitudinal depressions in the further set of depressions are arranged perpendicular to a further direction.

In a preferred variant of the electrical conductor, at least one or all of the following applies:
a. at least 50%, preferably at least 70%, and more preferably at least 85% of the macro protrusions have a width, measured along a further direction, in the range of 2.0 μm to 40.0 μm, preferably in the range of 5.0 μm to 25.0 μm, more preferably in the range of 7.0 μm to 20.0 μm, and further preferably in the range of 10.0 μm to 15.0 μm;
b. at least 50%, preferably at least 70%, and more preferably at least 85% of the micro protrusions have a width, measured along the further direction, in the range of 0.001 μm to 1.000 μm, preferably in the range of 0.001 μm to 0.700 μm, more preferably in the range of 0.001 μm to 0.500 μm, and further preferably in the range of 0.001 μm to 0.300 μm.

This preferred variant is a 3$^{rd}$ variant of the invention, that preferably depends on the 2$^{nd}$ variant of the invention. Furthermore, in this 3$^{rd}$ variant, all possible combination of the features a. and b. are preferred aspects of the variant. These combinations are e.g., a; b; a, b. c. In an aspect of the 3$^{rd}$ variant, it is preferred that the further direction is perpendicular to the first direction.

In a preferred variant of the electrical conductor, at least one or all of the following applies:
a. at least 50%, preferably at least 70%, and more preferably at least 85% of the longitudinal depressions in the first set of depressions have a ratio of a depth to a width that is in the range of 0.01 to 3.00, preferably in the range of 0.05 to 2.00, more preferably in the range of 0.10 to 1.50;
b. at least 50%, preferably at least 70%, and more preferably at least 85% of the longitudinal depressions in the further set of depressions have a ratio of a depth to a width that is in the range of 0.01 to 2.00, preferably in the range of 0.05 to 1, more preferably in the range of 0.10 to 0.80.

This preferred variant is a 4$^{th}$ variant of the invention, that preferably depends on any of the 1st to 3$^{rd}$ variants of the invention. Furthermore, in this 4th variant, all possible combination of the features a. and b. are preferred aspects of the variant. These combinations are e.g., a; b; a, b. In an aspect of the 4$^{th}$ variant, the ratio of the depth to the width of a longitudinal depression is calculated by dividing the depth of the longitudinal depression by the width of the longitudinal depression.

In a preferred variant of the electrical conductor, at least one or all of the following applies:
a. at least 50%, preferably at least 70%, and more preferably at least 85% of the longitudinal depressions in the first set of depressions are parallel to each other;
b. at least 50%, preferably at least 70%, and more preferably at least 85% of the longitudinal depressions in the further set of depressions are parallel to each other;
c. at least 50%, preferably at least 70%, and more preferably at least 85% of the longitudinal depressions in the first set of depressions are perpendicular to at least 50%, preferably at least 70%, and more preferably at least 85% of the longitudinal depressions in the further set of depressions.

This preferred variant is a 5$^{th}$ variant of the invention, that preferably depends on any of the 1$^{st}$ to 4$^{th}$ variants of the invention. Furthermore, in this 5$^{th}$ variant, all possible combination of the features a. to c. are preferred aspects of the variant. These combinations are e.g., a; b; c; a, b; a, c; b, c; a, b, c.

In a preferred variant of the electrical conductor, at least one or all of the following applies:
a. at least 50%, preferably at least 70%, and more preferably at least 85% of the longitudinal depressions in the first set of depressions have a depth that is in the range of 5.0 μm to 30.0 μm, preferably in the range of 8.0 μm to 20.0 μm, and more preferably in the range of 10.0 μm to 15.0;
b. at least 50%, preferably at least 70%, and more preferably at least 85% of the longitudinal depressions in the further set of depressions have a depth in the range of 1.0 μm to 18.0 μm, preferably in the range of 2.0 μm to 15.0 μm, and more preferably in the range of 4.0 μm to 12.0 μm.

This preferred variant is a 6th variant of the invention, that preferably depends on any of the 1st to 5th variants of the invention. Furthermore, in this 6th variant, all possible combination of the features a. and b. are preferred aspects of the variant. These combinations are e.g., a; b; a, b.

In a preferred variant of the electrical conductor, at least one or all of the following applies:
- a. at least 50%, preferably at least 70%, and more preferably at least 85% of the longitudinal depressions in the first set of depressions have a width in the range of 1.0 μm to 200.0 μm, preferably in the range of 5.0 μm to 80.0 μm, more preferably in the range of 5.0 μm to 50.0 μm, further preferably in the range of 8.0 μm to 20.0 μm, and even further preferably in the range of 10.0 μm to 15.0 μm;
- b. at least 50%, preferably at least 70%, and more preferably at least 85% of the longitudinal depressions in the further set of depressions have a width in the range of 1.0 μm to 200.0 μm, preferably in the range of 5.0 μm to 80.0 μm, more preferably in the range of 5.0 μm to 50.0 μm, further preferably in the range of 8.0 μm to 20.0 μm, and even further preferably in the range of 10.0 μm to 14.0 μm.

This preferred variant is a 7th variant of the invention, that preferably depends on any of the 1st to 6th variants of the invention. Furthermore, in this 7th variant, all possible combination of the features a. and b. are preferred aspects of the variant. These combinations are e.g., a; b; a, b.

In a preferred variant of the electrical conductor, at least one or all of the following applies:
- a. at least 50%, preferably at least 70%, and more preferably at least 85% of the longitudinal depressions in the first set of depressions is in the shape of a "V";
- b. at least 50%, preferably at least 70%, and more preferably at least 85% of the longitudinal depressions in the further set of depressions is in the shape of a "V".

This preferred variant is an 8th variant of the invention, that preferably depends on any of the 1st to 7th variants of the invention. Furthermore, in this 8th variant, all possible combination of the features a. and b. are preferred aspects of the variant. These combinations are e.g., a; b; a, b.

In a preferred variant of the electrical conductor, the electrically conducting polymer comprises
- a. poly(3,4-ethylenedioxythiophene) (PEDOT), a functionalized derivative of PEDOT, or a mixture thereof;
- b. at least one photoreactive component comprising an anionic photoreactive hydrophilic polymer, preferably comprising a polyacrylamide and a photoreactive group;
- c. at least one of the following: a polyacetylene, a poly(fluorene), a polyphenylene, a polyphenylene vinylene, a polypyrene, a polyazulene, a polynaphthalene, a poly(pyrrole), a polycarbazole, a polyindole, a polyazepine, a polyaniline, a polyacene, a polythiophene, a polythiophene vinylene, a poly(p-phenylene sulfide), a polypyridine, or functionalized derivatives, precursors or blends of two or more thereof.

This preferred variant is a 9th variant of the invention, that preferably depends on any of the 1st to 8th variants of the invention. Furthermore, in this 9th variant, all possible combination of the features a. to c. are preferred aspects of the variant. These combinations are e.g., a; b; c; a, b; a, c; b, c; a, b, c.

In a preferred variant of the electrical conductor, the first layer comprises a metal, a metal alloy, or a combination thereof. A preferred metal is selected from the group consisting of iron, silver, copper, nickel, palladium, platinum, gold, iridium, titanium, hafnium, niobium, tantalum, cobalt, chromium, zirconium, rhenium, tungsten, molybdenum, and combinations, e.g., mixtures, preferably alloys, of at least two of these metals. A particularly preferred metal is platinum. A particularly preferred alloy is a platinum alloy, with a platinum iridium alloy more particular preferred. A further example of an alloy is steel. This preferred variant is a 10th variant of the invention, that preferably depends on any of the 1st to 9th variants of the invention.

In a preferred variant of the electrical conductor, the at least one coating layer comprises at least 10 wt. %, preferably at least 25 wt. %, more preferably at least 50 wt. %, and particularly preferred at least 80 wt. %, based on the total weight of the at least one coating layer, of the electrically conducting polymer. This preferred variant is an 11th variant of the invention, that preferably depends on any of the 1st to 10th variants of the invention.

In a preferred variant of the electrical conductor, at least one or all of the following applies:
- a. the first layer has a thickness in the range of 1.0 μm to 160.0 μm, preferably in the range of 60.0 μm to 140.0 μm, and more preferably in the range of 80.0 μm to 120.0 μm;
- b. the at least one coating layer has a thickness in the range of 1.0 μm to 24.0 μm, preferably in the range of 9.0 μm to 21.0 μm, and more preferably in the range of 12.0 μm to 18.0 μm.

This preferred variant is a 12th variant of the invention, that preferably depends on any of the 1st to 11th variants of the invention. Furthermore, in this 12th variant, all possible combination of the features a. and b. are preferred aspects of the variant. These combinations are e.g., a; b; a, b.

In a preferred variant of the electrical conductor, the at least one coating layer is hydrophilic. This preferred variant is a 13th variant of the invention, that preferably depends on any of the 1st to 12th variants of the invention.

In a preferred variant of the electrical conductor, the at least one coating layer has a metal content of less than 10 wt-%, preferably less than 7 wt-%, and more preferably less than 5 wt-%, based on the weight of the at least one coating layer. This preferred variant is a 14th variant of the invention, that preferably depends on any of the 1st to 13th variants of the invention.

A fifteenth (15th) variant of the invention is a method for producing an electrical conductor, comprising the steps of
- a. providing
  - i. a first layer, wherein the first layer is electrically conducting,
  - ii. at least one laser beam,
  - iii. a removal means;
- b. operating the at least one laser beam to ablate the first layer, wherein the ablation
  - i. produces a first set of depressions in the first layer, wherein the first set of depressions comprises at least two longitudinal depressions;
  - ii. is performed over a time interval $T_1$;
- c. coating the first layer with at least one coating layer, wherein the at least one coating layer comprises an electrically conducting polymer;

wherein
the removal means is operated over a time interval $T_2$, and wherein the time intervals $T_1$ and $T_2$ at least partially overlap.

In an aspect of the 15th variant, it is preferred that the time intervals $T_1$ and $T_2$ overlap by at least 80%, more preferably by at least 90%, and further preferably by at least 95%. In another aspect of the 15th variant, it is preferred that $T_2 > T_1$.

In yet another aspect of the 15$^{th}$ variant, it is preferred that a starting point of $T_2$ is before a starting point of $T_1$. In yet another aspect of the 15$^{th}$ variant, it is preferred that an end point of $T_2$ is after an end point of $T_1$.

In a preferred variant of the method for producing an electrical conductor, the removal means is adapted and arranged to produce a flow of a gas, preferably air. This preferred variant is a 16th variant of the invention, that preferably depends on the 15$^{th}$ variant of the invention.

In a preferred variant of the method for producing an electrical conductor, the removal means is selected from the group consisting of a laser exhaust and a laser dust removal system. This preferred variant is a 17$^{th}$ variant of the invention, that preferably depends on any of the 15th to 16$^{th}$ variants of the invention.

In a preferred variant of the method for producing an electrical conductor, the method further comprises the step of operating the at least one laser beam to ablate the first layer, wherein
 A. the ablation
  i. produces a further set of depressions in the first layer, wherein the further set of depressions comprises at least two longitudinal depressions,
  ii. is performed over a time interval $T_3$; and
 B. the removal means is operated over a time interval $T_4$, and wherein the time intervals $T_3$ and $T_4$ at least partially overlap.

This preferred variant is an 18$^{th}$ variant of the invention, that preferably depends on any of the 15$^{th}$ to 17$^{th}$ variants of the invention. In an aspect of the 18$^{th}$ variant, it is preferred to perform the above step prior to coating the first layer with the at least one coating layer. In an aspect of the 18$^{th}$ variant, it is preferred that the time intervals $T_3$ and $T_4$ overlap by at least 80%, more preferably by at least 90%, and further preferably by at least 95%. In another aspect of the 18th variant, it is preferred that $T_4 > T_3$. In yet another aspect of the 18$^{th}$ variant, it is preferred that a starting point of $T_4$ is before a starting point of $T_3$. In yet another aspect of the 18$^{th}$ variant, it is preferred that an end point of $T_4$ is after an end point of $T_3$. In an aspect of the 18$^{th}$ variant, it is preferred that the time intervals $T_1$ and $T_3$ do not overlap. It is equally preferred that the time intervals $T_1$ and $T_3$ at least partially overlap.

In a preferred variant of the method for producing an electrical conductor, the removal means has a volume flow rate in the range of 150 m$^3$/h to 5000 m$^3$/h, preferably in the range of 150 m$^3$/h to 1500 m$^3$/h, and more preferably in the range of 250 m$^3$/h to 350 m$^3$/h. This preferred variant is an 19$^{th}$ variant of the invention, that preferably depends on any of the 15$^{th}$ to 18$^{th}$ variants of the invention.

In a preferred variant of the method for producing an electrical conductor, the removal means comprises at least one filter that is adapted and arranged to filter detached particulated material. This preferred variant is a 20$^{th}$ variant of the invention, that preferably depends on any of the 15th to 19$^{th}$ variants of the invention. In the 20$^{th}$ variant, it is preferred that the detached particulated material comprises material that has become detached from the first layer during ablation of the first layer.

In a preferred variant of the method for producing an electrical conductor, the method further comprises at least one or all of the following steps:
 a. increasing a depth of at least 50%, preferably at least 70%, and more preferably at least 85% of the longitudinal depressions in the first set of depressions by laser ablation;
 b. increasing a depth of at least 50%, preferably at least 70%, and more preferably at least 85% of the longitudinal depressions in the further set of depressions by laser ablation.

This preferred variant is a 21$^{st}$ variant of the invention, that preferably depends on any of the 15th to 20$^{th}$ variants of the invention. Furthermore, in this 21$^{st}$ variant, all possible combination of the features a. and b. are preferred aspects of the variant. These combinations are e.g., a; b; a, b. In an aspect of the 21$^{st}$ variant, it is preferred that the depths of the longitudinal depressions in the first set of depressions are increased prior to coating the first layer with the at least one coating layer. In another aspect of the 21$^{st}$ variant, it is preferred that the depths of the longitudinal depressions in the further set of depressions are increased prior to coating the first layer with the at least one coating layer. In yet another aspect of the 21$^{st}$ variant, it is preferred that the depths of the longitudinal depressions in the first set of depressions are increased either before, at least partially simultaneously, or after ablating the further set of depressions.

In a preferred variant of the method for producing an electrical conductor, at least one or all of the following applies:
 a. at least 50%, preferably at least 70%, and more preferably at least 85% of the longitudinal depressions in the first set are parallel to each other;
 b. at least 50%, preferably at least 70%, and more preferably at least 85% of the longitudinal depressions in the further set are parallel to each other;
 c. at least 50%, preferably at least 70%, and more preferably at least 85% of the longitudinal depressions in the first set are perpendicular to at least 50%, preferably at least 70%, and more preferably at least 85% of the longitudinal depressions in the further set.

This preferred variant is a 22$^{nd}$ variant of the invention, that preferably depends on any of the 15$^{th}$ to 21$^{st}$ variants of the invention. Furthermore, in this 22$^{nd}$ variant, all possible combination of the features a. to c. are preferred aspects of the variant. These combinations are e.g., a; b; c; a, b; a, c; b, c; a, b, c.

In a preferred variant of the method for producing an electrical conductor, the laser ablation is performed using a scanning velocity that is larger than 1000 mm/min, preferably a scanning velocity in the range of 1200 mm/min to 75 000 mm/min, more preferably a scanning velocity in the range of 1500 mm/min to 30 000 mm/min. This preferred variant is a 23$^{rd}$ variant of the invention, that preferably depends on any of the 15$^{th}$ to 22$^{nd}$ variants of the invention.

In a preferred variant of the method for producing an electrical conductor, the at least one laser beam is a pulsed laser beam. This preferred variant is a 24$^{th}$ variant of the invention, that preferably depends on any of the 15$^{th}$ to 23$^{rd}$ variants of the invention.

In a preferred variant of the method for producing an electrical conductor, the at least one laser beam has at least one or all of the following properties:
 a. a spectrum with a peak wavelength in the range of 250 nm to 2000 nm, preferably in the range of 500 nm to 1500 nm, and more preferably in the range of 800 nm to 1200 nm;
 b. a focal spot diameter in the range of 1 μm to 200 μm, preferably in the range of 2 μm to 100 μm, and more preferably in the range of 5 μm to 50 μm;
 c. a pulse repetition rate in the range of 1 kHz to 50 MHz, preferably in the range of 20 kHz to 1000 kHz, more preferably in the range of 50 kHz to 500 kHz, and further preferably in the range of 100 kHz to 200 kHz;

d. a pulse duration in the range of 100 fs to 20 ps, preferably in the range of 200 fs to 10 ps, and more preferably in the range of 500 fs to 1500 fs;

e. an energy per pulse in the range of 100 nJ to 5000 µJ, preferably in the range of 200 nJ to 1000 µJ, more preferably in the range of 500 nJ to 100 µJ, and further preferably in the range of 500 nJ to 20 µJ.

This preferred variant is a 25$^{th}$ variant of the invention, that preferably depends on any of the 15$^{th}$ to 24$^{th}$ variants of the invention. Furthermore, in this 25$^{th}$ variant, all possible combination of the features a. to e. are preferred aspects of the variant. These combinations are e.g., a; b; c; d; e; a, b; a, c; a, d; a, e; b, c; b, d; b, e; c, d; c, e; d, e; a, b, c; a, b, d; a, b, e; a, c, d; a, c, e; a, d, e; b, c, d; b, c, e; b, d, e; c, d, e; a, b, c, d; a, b, c, e; a, b, d, e; a, c, d, e; b, c, d, e; a, b, c, d, e. In an aspect of the 25$^{th}$ variant, it is preferred that the spot size is the length of a diameter of the spot. It is also preferred that a spot is a focal spot. It is more preferred that the spot is about circular. In an aspect of the 25$^{th}$ variant, it is preferred that the at least one laser beam is a pulsed laser beam. In this aspect, it is preferred that the fluence should be understood as the fluence per pulse.

In a preferred variant of the method for producing an electrical conductor, the at least one laser beam is obtainable from at least one solid-state laser. This preferred variant is a 26$^{th}$ variant of the invention, that preferably depends on any of the 15$^{th}$ to 25$^{th}$ variants of the invention. In an aspect of the 26$^{th}$ variant, a gain medium of the at least one solid-state laser is preferably a crystal. In this aspect, a preferred crystal is doped with neodym. In this aspect, a preferred neodym-doped crystal comprises yttrium. A preferred crystal which comprises yttrium is selected from the group consisting of Nd:YAG, 15 Nd:Y3Al5,O12, and Nd:YVO4, with Nd:YVO4 is particularly preferred.

In a preferred variant of the method for producing an electrical conductor, the at least one laser beam is a polarized laser beam. This preferred variant is a 27$^{th}$ variant of the invention, that preferably depends on any of the 15$^{th}$ to 26$^{th}$ variants of the invention.

In an aspect of the invention, it is preferred that the electrical conductor produced by any of the 15$^{th}$ to 27$^{th}$ variants is an electrical conductor according to any of the 1$^{st}$ to 14$^{th}$ variants.

A twenty-eighth (28$^{th}$) variant of the invention is an electrical conductor obtainable by a method according to the invention, preferably an electrical conductor obtainable according to the method of any of the 15$^{th}$ to 27$^{th}$ variants of the invention.

A twenty-ninth (29$^{th}$) variant of the invention is a use of an electrical conductor according to the invention, preferably the electrical conductor according to any of the 1$^{st}$ to 14$^{th}$, and 28$^{th}$ variants of the invention, for conveying an electrical signal, more preferably an electrical signal produced by a medical device.

A thirtieth (30$^{th}$) variant of the invention is a use of an electrical conductor according to the invention, preferably the electrical conductor according to any of the 1$^{st}$ to 14$^{th}$, and 28$^{th}$ variants of the invention, in an electrode, more preferably an electrode that is inserted into a body of a mammal, more preferably a body of a human. A preferred electrode is at least one or all of the following: a lead, a flexible electrode, an electrocorticography array, a catheter, or a combination of two or more thereof.

A thirty-first (31$^{st}$) variant of the invention is an electrode comprising at least one electrical conductor, preferably the electrical conductor according to any of the 1$^{st}$ to 14$^{th}$, and 28$^{th}$ variants of the invention, where the electrode is preferably an electrode that is inserted into a body of a mammal, more preferably a body of a human. A preferred electrode is at least one or all of the following: a lead, a flexible electrode, an electrocorticography array, a catheter, or a combination of two or more thereof. A preferred electrode consists of an electrical conductor, preferably an electrical conductor according to any of the 1$^{st}$ to 14$^{th}$, and 28$^{th}$ variants of the invention.

A thirty-second (32$^{nd}$) variant of the invention is a use of an electrode according to the invention, preferably the electrode according to the 31$^{st}$ variant of the invention, for conveying an electrical signal, more preferably an electrical signal produced by a medical device.

A thirty-third (33$^{rd}$) variant of the invention is a use of an electrode according to the invention, preferably the electrode according to the 31$^{st}$ variant of the invention, in an electrical device, preferably a medical device, more preferably a medical device used for at least one or all of the following: measuring an electrical signal (sensing), providing an electrical signal (stimulation), or both. A preferred medical device includes at least one or all of the following: a device for cardiac mapping, a cardiac defibrillator, a device for neuro-stimulation, a device for deep-brain stimulation, a device for neuro-sensing, or a combination of two or more thereof.

A thirty-fourth (34$^{th}$) variant of the invention is an electrical device that comprises an electrode according to the invention, preferably the electrode according to the 31$^{st}$ variant of the invention. It is preferred that the electrical device is a medical device. A preferred medical device is a medical device used for measuring an electrical signal (sensing), providing an electrical signal (stimulation), or both. A preferred medical device includes at least one or all of the following: a device for cardiac mapping, a cardiac defibrillator, a device for neuro-stimulation, a device for neuro-sensing, or a combination of two or more thereof. An example of a medical device used for both sensing and stimulation is a closed loop stimulation device.

A thirty-fifth (35$^{th}$) variant of the invention is a use of an electrical device according to the invention, preferably the electrical device according to the 34$^{th}$ variant of the invention, for measuring an electrical signal (sensing), providing an electrical signal (stimulation), or both. It is further preferred to use the electrical device for treating diseases like Parkinson's disease, epilepsy, back pain, and high blood pressure. It is also preferred to use the medical device for cardiac mapping, as a cardiac defibrillator, a neuro-stimulator, a neuro-sensor, or a combination of at least two or more thereof. An example of a medical device used for both sensing and stimulation is a closed loop stimulation device.

BRIEF DESCRIPTION OF THE DRAWINGS

FIG. 6 is a flow diagram illustrating the steps of a method according to the invention for producing an electrical conductor;

DETAILED DESCRIPTION OF THE INVENTION

Figure 1A:
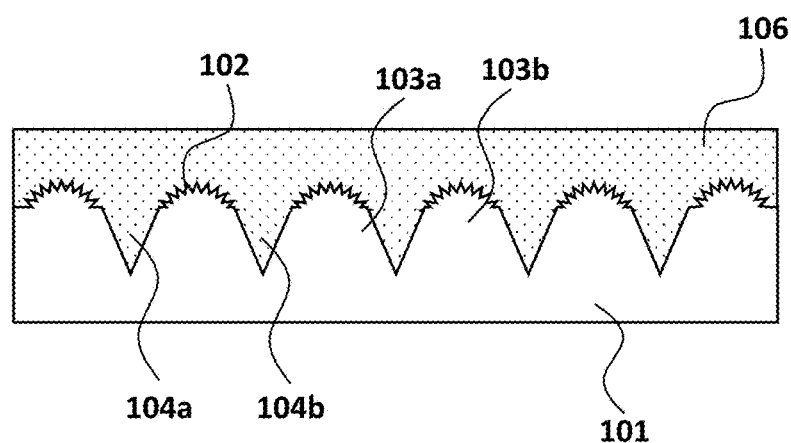
FIG. 1A is a schematic illustration of a cross-section of an electrical conductor according to the invention.

Further details regarding aspects of the invention are given below.

First Layer

In an aspect of the invention, it is preferred that the first layer comprises a biocompatible metal. The term "biocompatible" should be understood to mean a material which is considered by a person skilled in the art to be safe when being in contact with a living organism over a specific period of time (e.g., when used in an implantable medical device). A living organism is preferably a mammal, and more preferably a human. Whether a metal is biocompatible can be determined using the standard EN ISO 10993.

In an aspect of the invention, it is preferred that the first layer has a width in the range of 0.1 mm to 10.0 mm, more preferably in the range of 0.3 mm to 5.0 mm. In an aspect of the invention, it is preferred that the first layer has a length in the range of 0.1 mm to 20 mm, more preferably in the range of 0.3 mm to 5 mm. In an aspect of the invention, it is preferred that the first layer has a height in the range of 0.01 mm to 10.00 mm, more preferably in the range of 0.05 mm to 5.00 mm. In an aspect of the invention, it is preferred that the first layer has a diameter in the range of 0.01 mm to 10.00 mm, more preferably in the range of 0.05 mm to 5.00 mm. In an aspect of the invention, it is preferred that the first layer has a thickness in the range of 0.01 mm to 10.00 mm, more preferably in the range of 0.05 mm to 5.00 mm. E.g., the first layer is ring-shaped with a length of 3.0 mm and a thickness of 1.10 mm.

At Least One Coating Layer

An aspect of the invention relates to at least one coating layer that comprises an electrically conductive polymer. In an aspect of the invention, it is preferred that the electrically conductive polymer is cationic. In another aspect of the invention, it is preferred that the electrically conductive polymer comprises at least one or all of the following: a polyacetylene, a poly(vinyl alcohol), a poly(fluorene), a polypheny lene, a polypheny lene vinylene, a polypyrene, a polyazulene, a polynaphthalene, a poly (pyrrole), a polycarbazole, a polyindole, a polyazepine, a polyaniline, a polyacene, a polythiophene, a polythiophene vinylene, a poly(p-phenylene sulfide), a polypyridine, or functionalized derivatives, precursors or blends thereof.

In an aspect of the invention, it is preferred that the electrically conductive polymer comprises poly(3,4-ethylenedioxythiophene) (PEDOT), or a functionalized derivative thereof. For example, the electrically conductive polymer can be derived from 3,4-ethylenedioxythiophene (EDOT).

In an aspect of the invention, it is preferred that the electrically conductive polymer is derived from a functionalized derivative of EDOT selected from the group consisting of hydroxymethyl-EDOT, EDOT-vinyl, EDOT-ether allyl, EDOT-COOH, EDOT-MeOH, EDOT-silane, EDOT-vinyl, EDOT-acrylate, EDOT-sulfonate, EDOT-amine, EDOT-amide, and combinations thereof. As an example, the functionalized derivative of 3,4-ethylenedioxythiophene (EDOT) can be selected from the group consisting of hydroxymethyl-EDOT, EDOT-vinyl, EDOT-ether allyl, EDOT-acrylate, and combinations thereof.

In an aspect of the invention, it is preferred that the electrically conductive polymer comprises an anionic photoreactive cross-linking agent. In this aspect it is preferred that the cross-linking agents has at least two photoreactive groups. In a further aspect of the invention, it is preferred that the anionic photoreactive cross-linking agents comprise a compound of formula I: $X_i \sim Y \sim X_2$ where Y is a radical containing at least one acidic group or a salt of an acidic group; and $X_i$ and $X_2$ are each independently a radical containing a latent photoreactive group. Examples of a photoreactive group is an aryl ketone or a quinone. In another aspect of the invention, it is preferred that spacers are part of $X_i$ or $X_2$, preferably along with the latent photoreactive group.

In an aspect of the invention, it is preferred that in the compound of formula I, Y is a radical comprising at least one acidic group or salt thereof. Examples of acidic groups include, sulfonic acids, carboxylic acids, phosphonic acids, and the like. Examples of salts of such groups include sulfonate, carboxylate, and phosphate salts. As an example, the cross-linking agent can include a sulfonic acid or sulfonate group. In another aspect of the invention, it is preferred that such a photoreactive cross-linking agent is anionic. Examples of counter ions include alkali, alkaline earths metals, ammonium, protonated amines, and the like.

In an aspect of the invention, it is preferred that electrically conductive polymer comprises an anionic photoreactive hydrophilic polymer. In this aspect, it is preferred that the hydrophilic polymer is anionic. Examples of anionic hydrophilic polymers are homopolymers, copolymers, terpolymers, and the like. In another aspect of the invention, when the electrically conductive polymer comprises at least one anionic hydrophilic polymer, it is preferred that the anionic hydrophilic polymer is derivatized with photoreactive groups.

In a further aspect of the invention, it is preferred that the anionic hydrophilic polymer comprises polymers that comprise polyacrylamide and photoreactive groups ("Photo-PA"). In another aspect of the invention, it is preferred that the anionic hydrophilic polymer comprises polyacrylamide and sulfonate groups. For example, the anionic hydrophilic polymer comprises acrylamido-2-methylpropanesulfonate groups (AMPS) and polyethylene glycol segments.

The phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Unless otherwise stated, it is preferred that references to photoreactive groups herein shall also include the reaction products of the photoreactive groups.

In an aspect of the invention, it is preferred that photoreactive groups are chosen to be responsive to various portions of actinic radiation. For example, groups can be chosen that can be photoactivated using either ultraviolet or visible radiation. Examples of photoreactive groups include, azides, diazos, diazirines, ketones, and quinones. In yet another aspect of the invention, it is preferred that photoreactive group comprises an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinone such as, for example, anthraquinone.

Electrically conductive polymers are well-known to the skilled person, and are commercially available under the tradenames Orgacon®, obtainable from Agfa-Gevaert N.V. (Belgium), or Amplicoat®, obtainable from Heraeus Deutschland GmbH & Co. KG (Germany).

In another aspect of the invention, it is preferred that the at least one coating layer comprises a biocompatible polymer. In yet another aspect of the invention, it is also preferred that the at least one coating layer is hydrophilic. A "hydrophilic" material is defined as a material that has a water contact angle that is below 90°.

In another aspect of the invention, it is preferred that the at least one coating layer has a water contact angle that is in the range of 10° to 30°, preferably in the range of 15° to 25°, and more preferably in the range of 19° to 22°. In yet another aspect of the invention, it is preferred that the at least one coating layer has a surface energy that is in the range of 35 mN/m to 55 mN/m, more preferably in the range of 40 mN/m to 50 mN/m, and further preferably in the range of 42 mN/m to 46 mN/m.

Electrical Conductor

In an aspect of the invention, it is preferred that the electrical conductor has a shape of a known electrode for a medical device. In this aspect, it is preferred that the electrical conductor has the shape of a lead for a medical device. Examples of preferred shapes are cylindrical, ring-shaped, flat, spherical, needle-like, cubic, rectangular, or a combination of two or more thereof. A ring-shape is particularly preferred.

In another aspect of the invention, it is preferred that the electrical conductor has at least one dimension of a known electrode for a medical device. In an aspect of the invention, it is preferred that the electrical conductor has a width in the range of 0.1 mm to 30.0 mm, more preferably in the range of 0.1 mm to 20.0 mm, and further preferably in the range of 0.1 mm to 10.0 mm. In another aspect of the invention, it is preferred that the electrical conductor has a diameter in the range of 0.1 mm to 30.0 mm, more preferably in the range of 0.1 mm to 20.0 mm, and further preferably in the range of 0.1 mm to 10.0 mm. In an aspect of the invention, it is preferred that the electrical conductor has a length in the range of 0.1 mm to 60.0 mm, more preferably in the range of 0.1 mm to 40.0 mm, and further preferably in the range of 0.1 mm to 20.0 mm. In an aspect of the invention, it is preferred that the electrical conductor has a height in the range of 0.1 mm to 30.0 mm, more preferably in the range of 0.1 mm to 20.0 mm, and further preferably in the range of 0.1 mm to 10.0 mm.

In a further aspect of the invention, it is preferred that the electrical conductor has a water contact angle that is in the range of 10° to 30°, preferably in the range of 15° to 25°, and more preferably in the range of 19° to 22°. In another aspect of the invention, it is preferred that the electrical conductor has a surface energy that is in the range of 35 mN/m to 55 mN/m, more preferably in the range of 40 mN/m to 50 mN/m, and further preferably in the range of 42 mN/m to 46 mN/m.

First Direction and Further Direction

In an aspect of the invention, it is preferred that a first direction is along either a length, a width, or a circumference of the electrical conductor. In another aspect of the invention, it is preferred that a further direction is along either a length, a width, or a circumference of the electrical conductor. In a further aspect of the invention, it is preferred that the further direction is perpendicular to the first direction.

Macro Protrusions

In an aspect of the invention, it is preferred that the macro protrusions are formed by laser ablation of the first layer. In a further aspect of the invention, it is preferred that at least 50%, more preferably at least 70%, and further preferably at least 85% of the macro protrusions have, to a first approximation, a shape selected from the group consisting of: a straight line, a waved line, a square, a rectangle, a grooved rectangle, a rhombus, a parallelogram, and a triangle.

Micro Protrusions

In an aspect of the invention, it is preferred that less than 50%, more preferably less than 30%, and further preferably less than 15% of the micro protrusions of the electrical conductor have a width, measured along a first direction, that is in the range of 1.0 µm to 2.0 µm, preferably in the range of 0.5 µm to 1.0 µm, and more preferably in the range of 0.1 µm to 1.0 µm. In another aspect of the invention, it is preferred that less than 50%, more preferably less than 30%, and further preferably less than 15% of the micro protrusions of the electrical conductor have a width, measured along a further direction, that is in the range of 1.0 µm to 2.0 µm, preferably in the range of 0.5 µm to 1.0 µm, and more preferably in the range of 0.1 µm to 1.0 µm.

Longitudinal Depressions

In an aspect of the invention, it is preferred that a set of depressions comprises at least 2, more preferably at least 10, further preferably at least 50, an even further preferably at least 200 longitudinal depressions. In another aspect of the invention, it is preferred that a set of depressions comprises in the range of 10 to 1 000 000 longitudinal depressions.

In another aspect of the invention, it is preferred that the longitudinal depressions are in the shape of a "V". In this aspect it is preferred that the longitudinal depressions are, to a first approximation, in the shape of a "V". In another aspect of the invention, it is preferred that the longitudinal depressions are in the shape of a "U". In this aspect it is preferred that the longitudinal depressions are, to a first approximation, in the shape of a "U".

In an aspect of the invention, the first layer preferably comprises a first set of depressions and a further set of depressions. In this aspect, it is preferred that the longitudinal depressions in the first set of depressions cross the longitudinal depressions in the further set of depressions at an angle. E.g., an angle of 90° leads to the formation of macro protrusions that are, to a first approximation, square- or rectangular-shaped. E.g., an angle of 60° or 120° leads to the formation of macro protrusions that are, to a first approximation, rhombus- or diamond-shaped.

In an aspect of the invention, the first layer preferably comprises a first set of depressions, a further set of depressions, and an even-further set of depressions. In this aspect, it is preferred that the longitudinal depressions in the different sets of depressions cross each other at an angle, e.g., an angle of 60° or 120°. This leads to the formation of macro protrusions that are, to a first approximation, triangular.

In an aspect of the invention, a length of a longitudinal depression is preferably at least 100 μm, more preferably of at least 250 μm, and further preferably at least 45 mm. E.g., the longitudinal depressions have a length in the range of 100 μm to 50 mm. E.g., the longitudinal depressions have a length in the range of 250 μm to 50 mm.

Width and Depth of Longitudinal Depressions

In an aspect of the invention, it is preferred to measure a width of a longitudinal depression in the first set of depressions along the first direction. In another aspect of the invention, it is preferred to measure a depth of a longitudinal depression in the first set of depressions perpendicular to the first direction. In an aspect of the invention, it is preferred to measure a width of a longitudinal depression in the further set of depressions along the further direction. In another aspect of the invention, it is preferred to measure a depth of a longitudinal depression in the further set of depressions perpendicular to the further direction.

Laser Beam and Laser Ablation

Lasers for producing the laser beams suited to the present invention are well-known to a person skilled in the art. Such lasers are commercially available from e.g., Photonics Industries International, Inc (USA), or Trumpf GmbH and Co. KG (Germany).

The peak wavelength of a spectrum is a local maximum, preferably in addition a global maximum, of the spectrum. A preferred peak wavelength is a laser wavelength, i.e., a main wavelength of a laser output. The laser wavelength may be a lasing wavelength of a gain medium of the laser or a wavelength which is obtained by a non-linear optical effect, such as frequency doubling, from the lasing wavelength.

In an aspect of the invention, it is preferred that the energy density of the at least one laser beam used for the laser ablation of the first layer is higher than the laser ablation threshold of the first layer.

Laser ablation refers to a laser ablation process having a laser scan path, i.e., a scan line, wherein a start point of the scan line is preferably at least 100 μm (e.g., 100 μm to 50 mm), and more preferably at least 250 μm (e.g., 250 μm to 50 mm), away from an end point of the scan path.

In an aspect of the invention, it is preferred that the distance between scan lines is in the range of 1 μm to 200 μm, more preferably in the range of 5 μm to 80 μm, and further preferably in the range of 10 μm to 50 μm. In an aspect of the invention, if pairs of scan lines are used, it is preferred that the distance between neighboring pairs of scan lines is in the range of 1 μm to 200 μm, more preferably in the range of 5 μm to 80 μm, and further preferably in the range of 10 μm to 50 μm. In an aspect of the invention, if triplets of scan lines are used, it is preferred that the distance between neighboring triplets of scan lines is in the range of 1 μm to 200 μm, more preferably in the range of 5 μm to 80 μm, and further preferably in the range of 10 μm to 50 μm.

In an aspect of the invention, it is preferred to use a removal means during ablation of the first layer. This is, e.g., for the laser ablation of the first set of depressions, the laser ablation of the further set of depressions, increasing the depth of the first set of depressions using laser ablation, and increasing the depth of the further set of depressions using laser ablation. In this aspect, it is preferred that the time interval over which the removal means is used, $T_r$, at least partially overlaps with the time interval over which the laser ablation occurs, $T_a$. In this aspect, it is more preferred that that the time intervals $T_r$ and $T_a$ overlap by at least 80%, more preferably at least 90%, and further preferably at least 95%. In a related aspect, it is preferred that $T_r > T_a$. In yet another aspect, it is preferred that a starting point of $T_r$ is before a starting point of $T_a$. In yet another, it is preferred that an end point of $T_r$ is after an end point of $T_a$.

Removal Means

In an aspect of the invention, it is preferred that the removal means is adapted and arrange to remove at least one or all of the following: airborne pollutants, dust, and laser fume, preferably laser fume resulting from laser ablation of a first layer.

In an aspect of the invention, it is preferred that the removal means comprises at least one opening. In this aspect it is preferred that the at least one opening is adapted and arranged to allow gas to flow into the removal means. In another aspect of the invention, it is preferred that the at least one opening is elongated, e.g., in the form of an arm. In another aspect of the invention, it is preferred that a distance between the at least one opening and the first layer, during laser ablation of the first layer, is in the range of 10 cm to 50 cm, more preferably in the range of 20 cm to 40 cm, and further preferably in the range of 25 cm to 35 cm.

Removal means suitable to the present invention are well-known in the art. Suitable removal means are commercially available from, e.g., ULT AG (Germany), and BOFA International Ltd (UK).

Electrode and Medical Device

An aspect of the invention relates to an electrode that comprises at least one electrical conductor according to the invention. In this aspect, it is preferred that the electrode is suitable for use in an implantable medical device, and more preferably an active implantable medical device (AIMD). In another aspect of the invention, a preferred electrode according to the present invention is suitable for use in a temporary or short-term used medical device such as a catheter. In another aspect of the invention, it is preferred that the electrode is suitable for use in a lead for a medical device.

Another aspect of the invention relates to medical device comprising at least one electrode according to the present invention. In this aspect, it is preferred that the medical device is an implantable medical device, and more preferably an AIMD. In another aspect of the invention, it is preferred that the medical device is a temporary or short-term used medical device, such as a catheter. In yet another aspect of the invention, it is preferred that the medical device is a lead for at least one or all of the following: an active implantable medical device, an implantable device, a temporary, a short-term used medical device.

Preferred AIMDs are, for example, cardiac pacemakers, cardiac defibrillators, neurostimulators and/or neuromodulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. An example of a preferred medical device is a neuromodulator.

The figures serve to exemplify the present invention and should not be viewed as limiting the invention. The figures are not drawn to scale.

DESCRIPTION OF FIGURES

FIG. 1A shows a schematic illustration of a cross-section of an electrical conductor 100 according to the invention.

The electrical conductor 100 has a first layer 101, wherein the first layer 101 has micro protrusions 102 that are arranged on macro protrusions, e.g., 103a and 103b. The first layer 101 also has a first set of depressions that comprises longitudinal depressions, e.g., 104a and 104b. The longitudinal depressions 104 are, to a first approximation, in the form of a "V". FIG. 1A also shows that the macro protrusions 103 and the longitudinal depressions 104 are arranged in an alternating pattern. The first layer 101 is also coated with a coating layer 106, wherein the coating layer 106 touches the first layer 101.

Figure 1B:
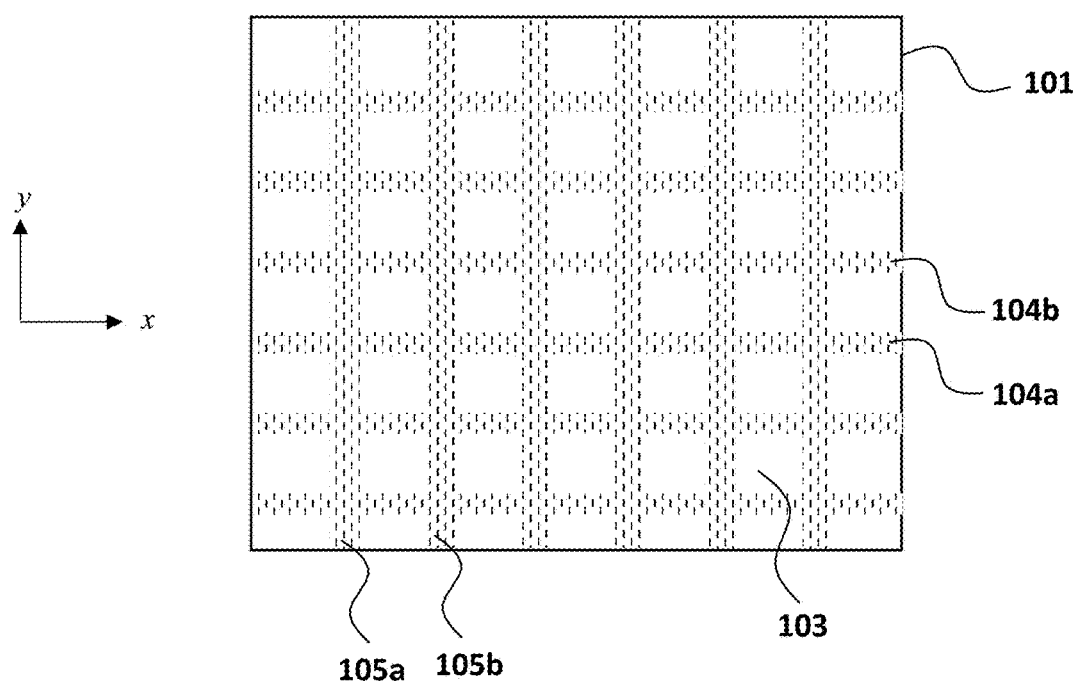
FIG. 1B is a schematic illustration a first layer according to the invention with longitudinal depressions, viewed from above.

FIG. 1B shows a schematic illustration of the first layer 101 viewed from above. A first set of depressions that comprises longitudinal depressions are arranged along a further direction, i.e., the x-axis. Examples of the longitudinal depressions in the first set of depressions are 104a and 104b. It can further be seen that the longitudinal depressions of the first set of depressions 104 are parallel to each other. Furthermore, a width of a longitudinal depression in the first set of depressions 104 is measured along a first direction (the y-axis). FIG. 1B also shows a further set of depressions that comprises longitudinal depressions that are arranged along the first direction, i.e., the y-axis. Examples of the longitudinal depressions in the further set of depressions are 105a and 105b. It can further be seen that the longitudinal depressions of the further set of depressions 105 are parallel to each other, as well as being perpendicular to the longitudinal depressions of the first set of depressions 104. Furthermore, a width of a longitudinal depression in the further set of depressions 105 is measured along a further direction (the x-axis).

FIG. 2 show greyscale images 200 of laser scanning microscopy of a first layer 201 (according to the present invention). The first layer 201, comprising a Pt/Ir alloy, has been laser ablated to produce a first set of depressions that comprises longitudinal depressions 204. FIG. 2 further show that the first set of depressions extends along the x-axis, and are parallel to each other. As a result of the laser ablation, macro protrusions 203 are formed.

Figure 2A:
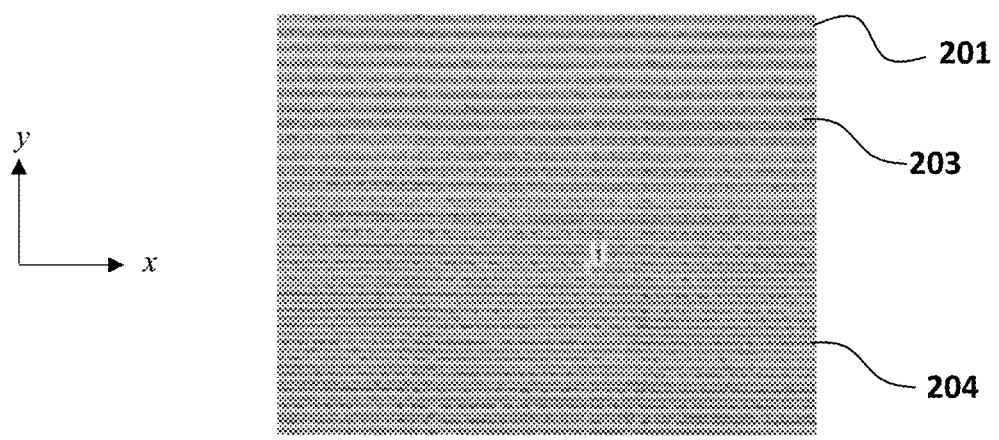
FIGS. 2A to 2D are greyscale images of laser scanning microscopy of the first layer according to the invention.
Figure 2B:
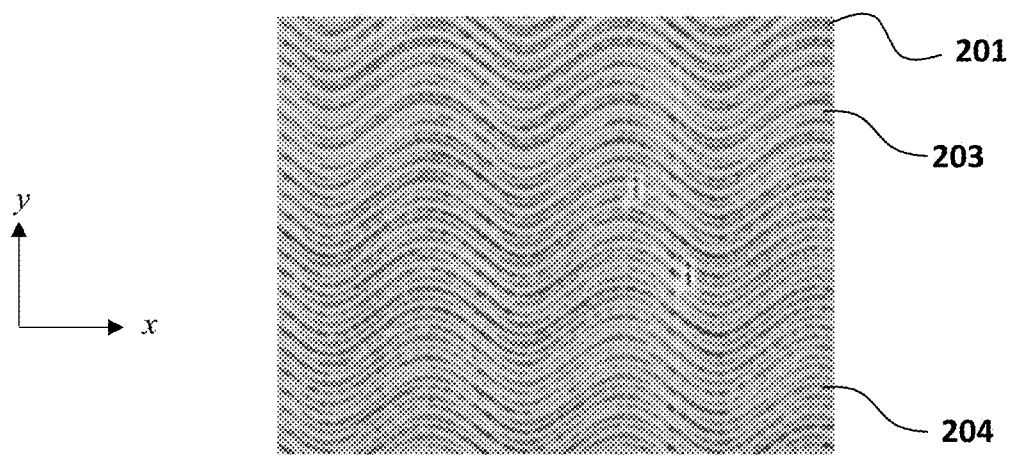

FIG. 2A shows that the longitudinal depressions 204 in the first set of depressions are straight lines. For the ablation in FIG. 2A, the distance between scan lines was 20 µm. This resulted in depths of the longitudinal depressions 204 that range from 11 µm to 14 µm (mean: 12 µm). FIG. 2B shows that the longitudinal depressions 204 in the first set of depressions are waved lines. Although the longitudinal depressions 204 are waved, they are still parallel to each other. For the ablation in FIG. 2B, the distance between scan lines was 20 µm. This resulted in depths of the longitudinal depressions 204 that range from 9 µm to 12 µm (mean: 10 µm).

Figure 2C:
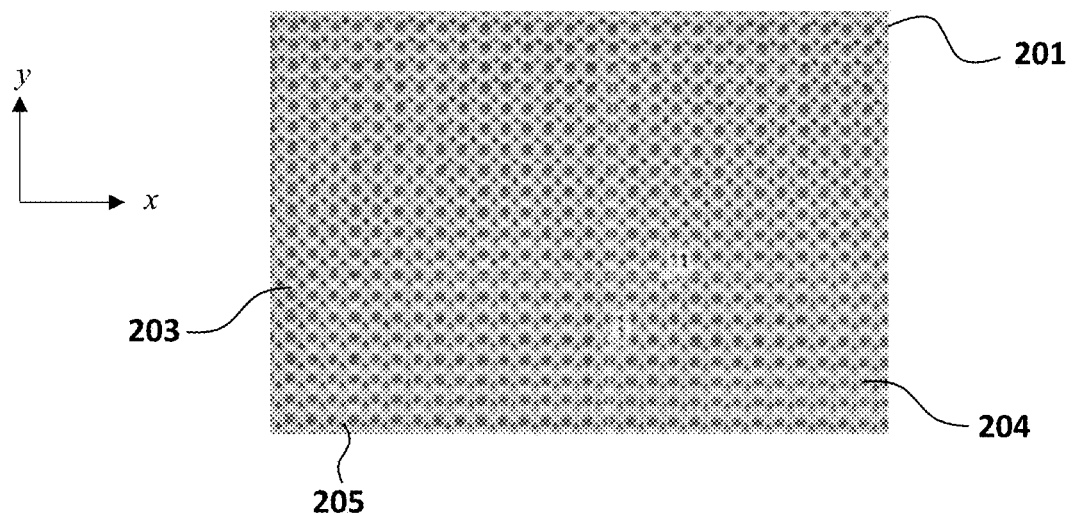

FIG. 2C shows that, apart from the first set of depressions 204 which extends along the direction of the x-axis, the first layer 201 also has further set of depressions 205 which extends along the direction of the y-axis. The longitudinal depressions 205 in the further set of depressions are parallel to each other, as well as perpendicular to the longitudinal depressions 204 in the first set of depressions. For the ablation in FIG. 2C, the distance between scan lines along both the x- and the y-direction was 20 µm. This resulted in the formation of macro protrusions 203 that are, to a first approximation, square. Furthermore, the depths of the longitudinal depressions, in both the first set of depressions 204 and the further set of depressions 205, is in the range of 8 µm to 14 µm (mean: 11 µm).

Figure 2D:
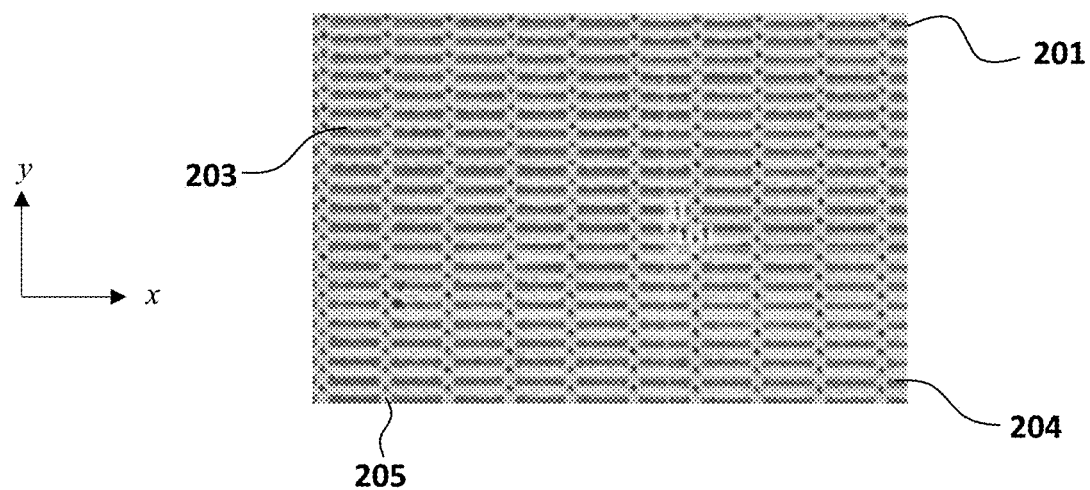

FIG. 2D shows that, apart from the first set of depressions 204 which extends along the direction of the x-axis, the first layer 201 also has further set of depressions 205 which extends along the direction of the y-axis. The longitudinal depressions 205 in the further set of depressions are parallel to each other, as well as perpendicular to the longitudinal depressions 204 in the first set of depressions. For the ablation in FIG. 2D, the distance between scan lines along the x-direction was 20 µm, while the distance between scan lines along the y-direction was 60 µm. This resulted in the formation of macro protrusions 203 that are, to a first approximation, rectangular.

Furthermore, the depths of the longitudinal depressions, in both the first set of depressions 204 and the further set of depressions 205, is in the range of 10 µm to 12 µm (mean: 11 µm).

FIG. 3 show scanning electron microscope images 300 of a laser-ablated, platinum/iridium first layer 301 (according to the present invention). FIG. 3 shows the images of the first layer 301 at different order of magnitudes. The first layer 301 has been laser ablated to produce a first set of depressions along a further direction, the x-axis. The first set of depressions comprise longitudinal depressions, e.g., 304a and 304b. The first layer 301 has also been laser ablated to produce a further set of depressions along a first direction, the y-axis. The further set of depressions comprise longitudinal depressions, e.g., 305a and 305b. As a result of the laser ablation, macro protrusions 303 are formed. During the ablation of the first layer 301, a laser exhaust was used.

Figure 3A:
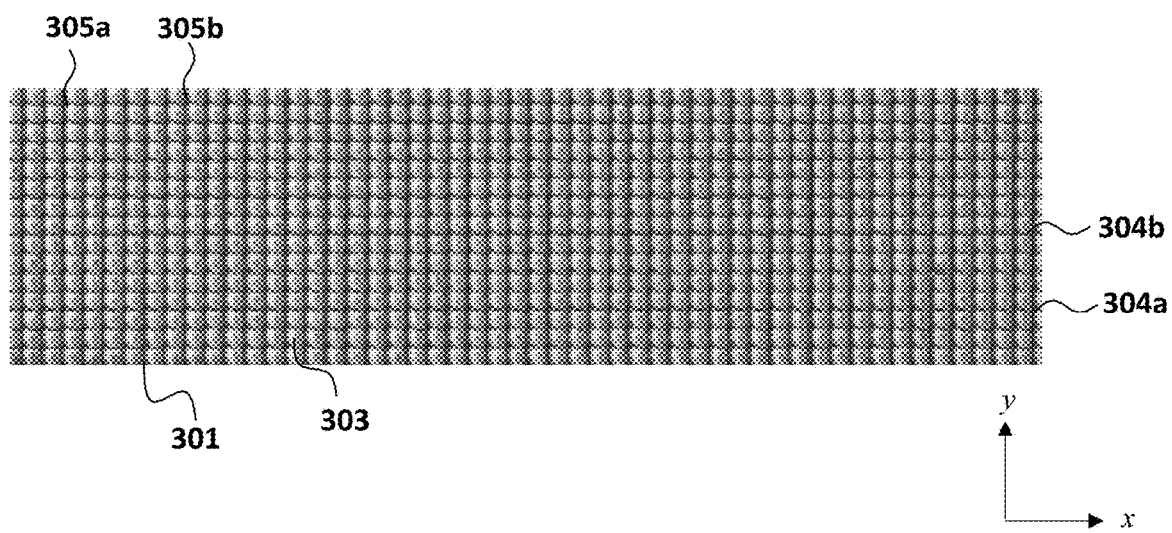
FIGS. 3A to 3D are scanning electron microscope images of a laser-ablated platinum/iridium first layer according to the invention in different order of magnitudes.

FIG. 3A shows that the longitudinal depressions 304 in the first set of depressions are parallel to each other. FIG. 3A also shows that the longitudinal depressions 305 in the further set of depressions are parallel to each other, as well as being perpendicular to the longitudinal depressions 304 in the first set of depressions. For the ablation in FIG. 3A, the distance between scan lines along both the x- and the y-direction was 45 µm. Furthermore, the depths of the longitudinal depressions, in both the first set of depressions 304 and the further set of depressions 305, have a mean of 42 µm.

Figure 3B:
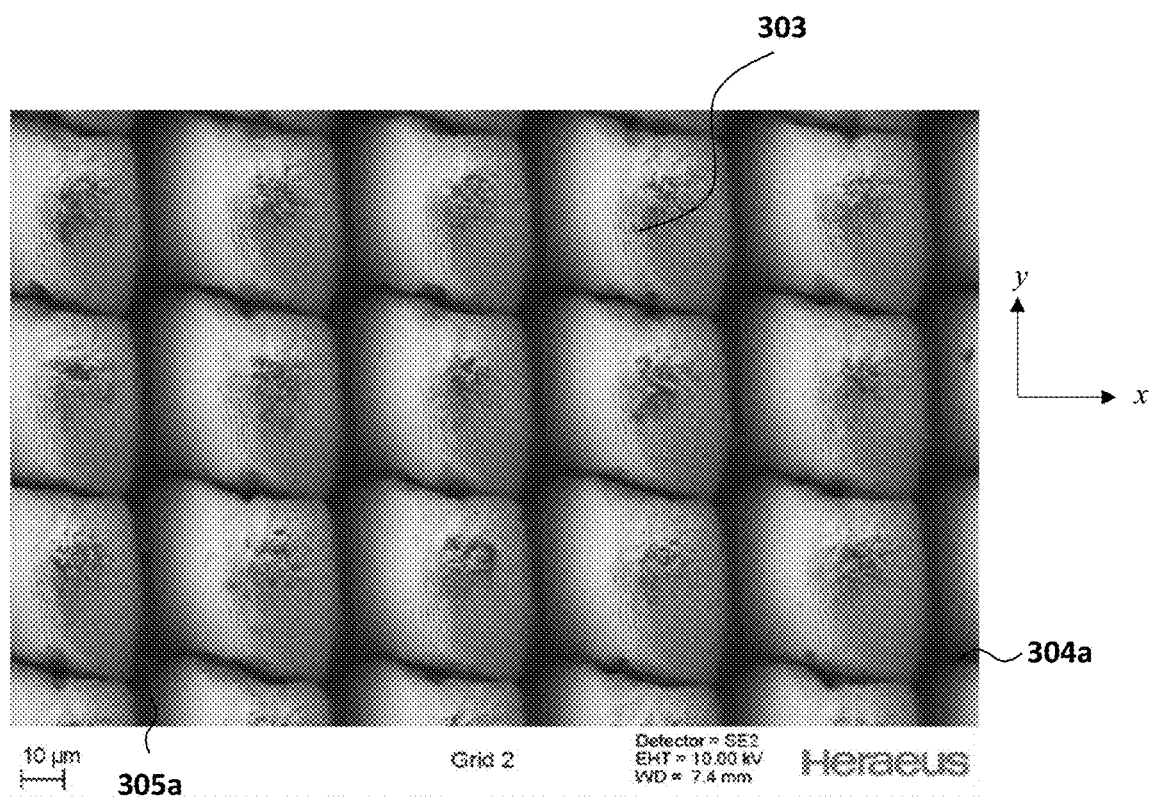
Figure 3C:
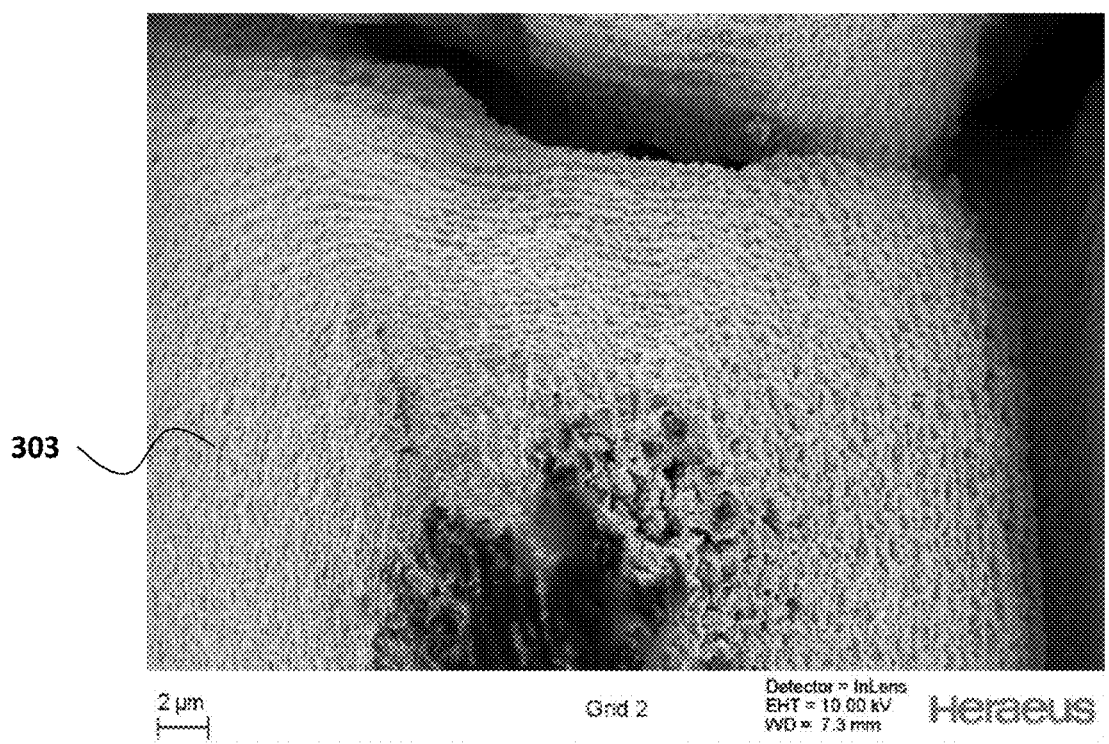
Figure 3D:
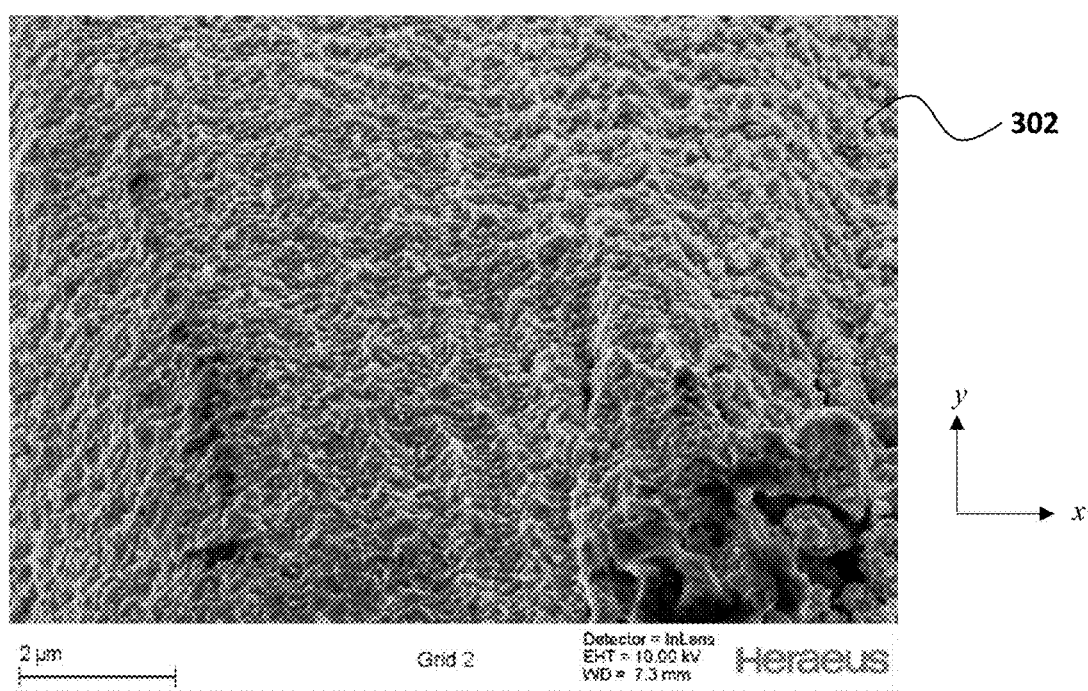

FIG. 3B shows that the macro protrusions 303 are, to a first approximation, square. FIGS. 3C and 3D are enlargements of one of the macro protrusions 303, which show micro protrusions 302 that are arranged on the macro protrusion 303. A width of the micro protrusions 302, measured along the x-axis, is less than 1 µm. Furthermore, more than 70% of the micro protrusions have a width, measured along the x-axis, that is less than 0.5 µm.

Figure 4A:
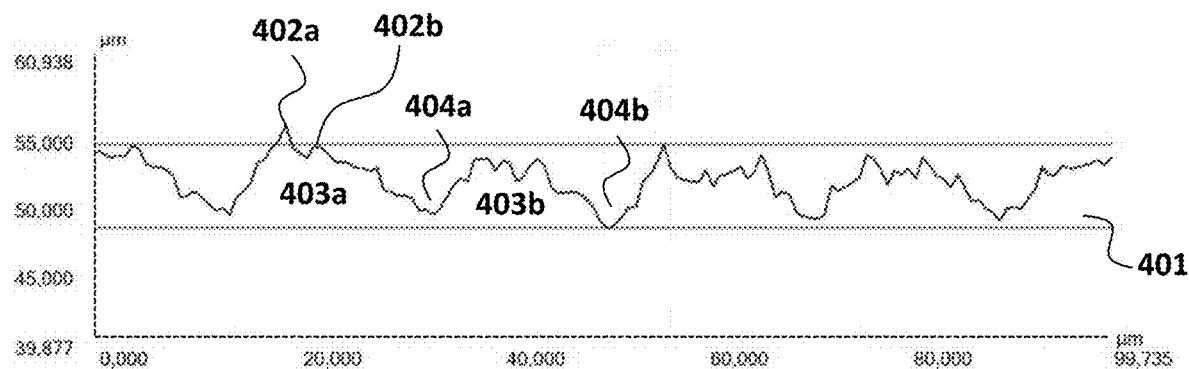
FIG. 4A is a cross-sectional scan of a first layer according to the invention.

FIG. 4A shows a cross-sectional scan 400 of a first layer according to the invention. The cross-sectional scan 400 was taken along a first direction (the y-axis). FIG. 4A shows that the first layer 401 has macro protrusions, e.g., 403a and 403b, as well as longitudinal depressions, e.g., 404a and 404b, that from part of a first set of depressions. FIG. 4A also shows that the macro protrusions 403 have micro protrusions, e.g., 402a and 402b, arranged on the macro protrusions 403.

Figure 4B:
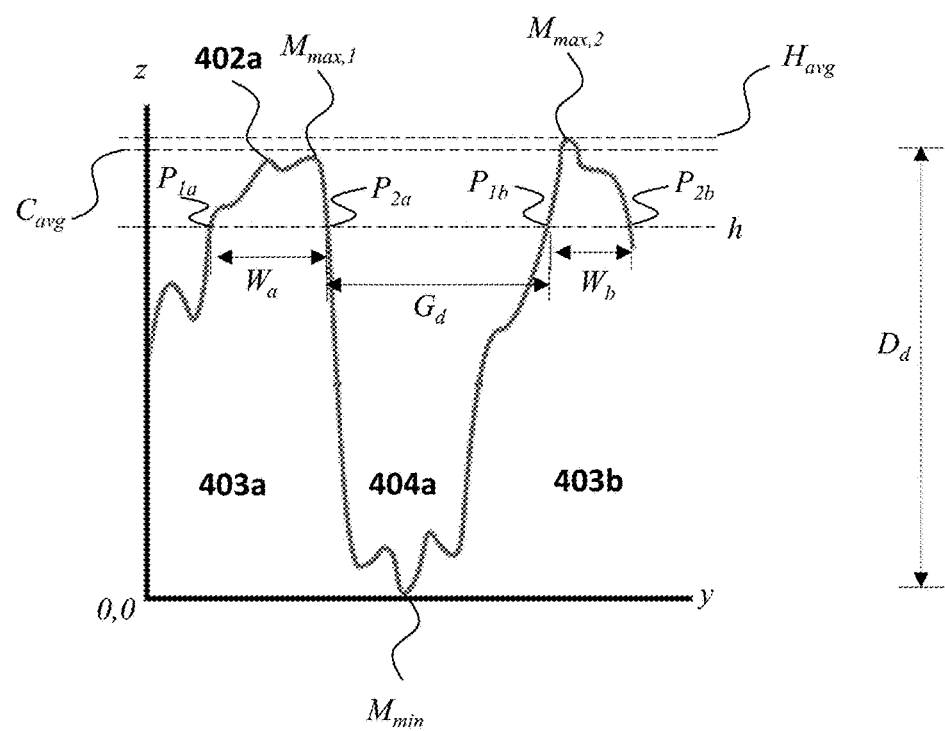
FIGS. 4B and 4C are schematic illustrations showing how different dimensions of the longitudinal depressions, micro protrusions, and macro protrusions are measured.
Figure 4C:
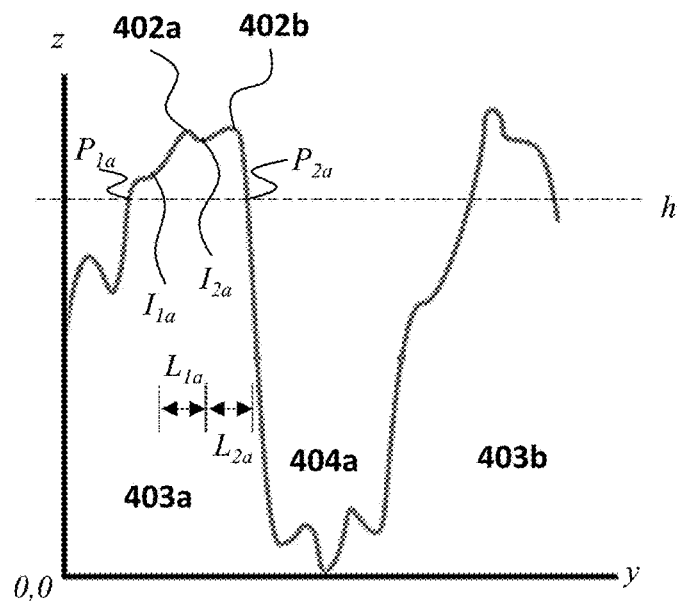

FIGS. 4B and 4C are schematic illustrations showing how different dimensions of the longitudinal depressions, micro protrusions, and macro protrusions are measured. Furthermore, FIGS. 4B and 4C are schematic illustrations of a cross-sectional scan of the first layer. FIGS. 4B 4C show how the dimensions of the protrusions and longitudinal depressions, along a specific direction, are measured. In FIGS. 4B and 4C, the dimensions are measured along the first direction. While illustrated for the first direction, the procedure is the same for measuring distances along a further direction.

FIGS. 4B and 4C show two macro protrusions 403a and 403b, as well as the longitudinal depression 404a. FIGS. 4B and 4C also shows micro protrusions, e.g., 402a and 402b, that are arranged on the macro protrusions 403. To measure the dimensions, the cross-sectional scan is arranged on a y-z graph such that the lowest point, $M_{min}$, of the cross-sectional scan is on the z=0 line, i.e., touches the y-axis. This lowest point $M_{min}$ is a global minimum of the cross-sectional scan. The height of a macro protrusion is defined as the highest point of the macro protrusion, as measured from the y-axis. In FIG. 4B, the highest points $W_{max,1}$ and $M_{max,2}$, are shown for the two macro protrusions 403a and 403b, respectively. These highest points are local maxima of the cross-sectional scan.

In order to measure the width of a macro protrusion, the average height, $H_{avg}$, of all the macro protrusions in the cross-sectional scan is first calculated. This average height is indicated in FIG. 4B by a dashed-line. The next step is to calculate a height h, which is calculated as $$h=0.85*H_{avg}.$$

A line, corresponding to the value of h, is then drawn on the y-z graph, parallel to the y-axis (see FIG. 4B). The two points on the y-z graph where this h line intersects with a macro protrusion defines the edges of the macro protrusion. FIG. 4B shows that for the macro protrusion 403a, the two intersection points are $P_{1a}$ and $P_{2a}$, while the two intersection points for macro protrusion 403b are $P_{1b}$ and $P_{2b}$. The width of a macro protrusion is then defined as the distance between the two intersection points, i.e., the distance $W_a$ for macro protrusion 403a and the distance Wb macro protrusion 403b.

FIG. 4B also shows how the width and depth of a longitudinal depression is defined. The width of the longitudinal depression, along the first direction, is defined as the distance between the closest intersection points of two neighboring macro protrusions. Here the two neighboring macro protrusions are taken as the macro protrusions on either side of the longitudinal depression. In FIG. 4B the two neighboring macro protrusions are 403a and 403b, and the closest intersection points are $P_{2a}$ and $P_{1b}$. The width of longitudinal depression 404a is therefore defined as the distance Gd.

To calculate the depth of a longitudinal depression, the average height of the two neighboring macro protrusions, $C_{avg}$, is calculated. Here the two neighboring macro protrusions are again taken as the macro protrusions on either side of the longitudinal depression. The depth of a longitudinal depression is then measured as the distance between the y-axis and the average height $C_{avg}$. The depth $D_d$ of longitudinal depression 404a is shown in FIG. 4B.

The micro protrusions are defined as only those protrusions that are arranged between the two edges of a macro protrusion. Furthermore, a width of a micro protrusion along a direction is defined as the distance between two neighboring inflection points on either side of the micro protrusion, or for a micro protrusion at the edge of a macro protrusion, between an inflection point and the edge of the macro protrusion. This is shown in FIG. 4C. The micro protrusion 402a is located between the two inflection points $I_a$ and $I_{1a}$, and has a width $L_{1a}$. The micro protrusion 402b is located between the inflection point $I_{2a}$ and the edge $P_{2a}$ of the macro protrusion 403a, and has a width $L_{2a}$.

Figure 5:
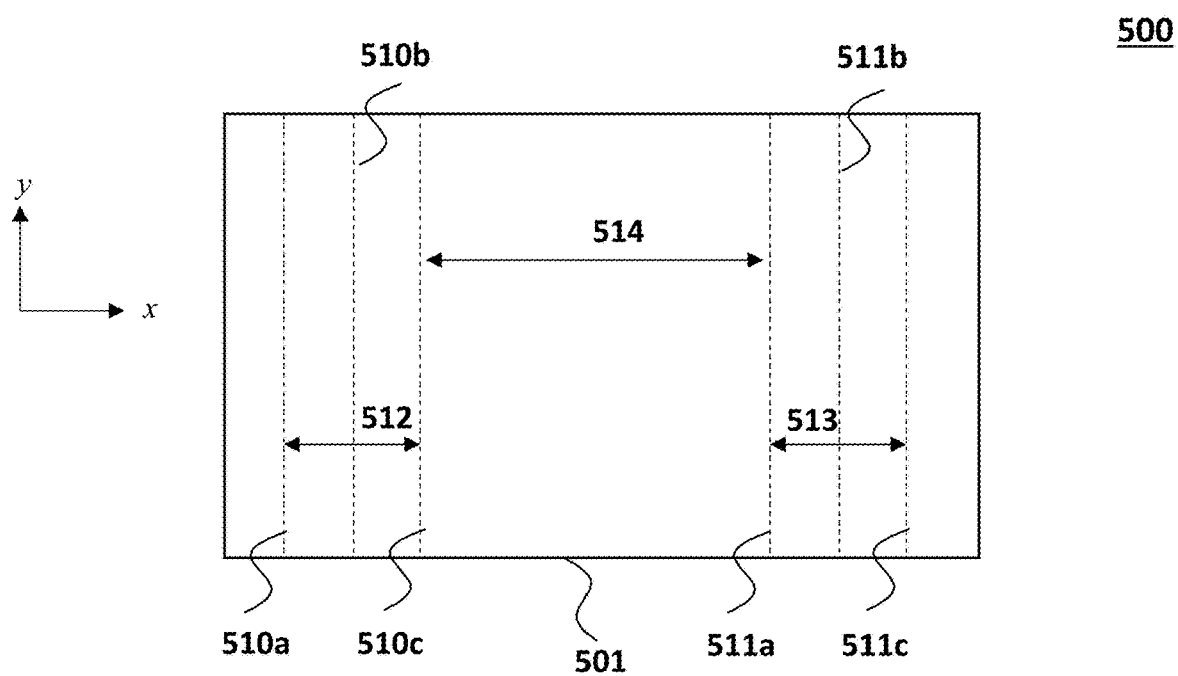
FIG. 5 is a schematic illustration showing how distance between scan lines are calculated.

FIG. 5 shows a schematic illustration of how the distance 500 between neighboring triplets of scan lines are calculated. Shown is a first layer 501, a first triplet of scan lines 510, consisting of the scan lines 510a, 510b, 510c, and a further triplet of scan lines 511, consisting of the scan lines 511a, 511b, 511c. The scan lines are indicated by the dashed lines. Furthermore, all scan lines are along the y-axis. Neighboring triplets of scan lines should be understood to mean that there are no other triplets of scan lines, parallel to the neighboring triplets of scan lines, between the neighboring triplets of scan lines. In FIG. 5, a width of the scan lines forming the first triplet of scan lines 510 is indicated by 512, while a width of the scan lines forming the further triplet of scan lines 511 is indicated by 513. The distance between the neighboring triplets of scan lines is indicated by 514. The above illustration also holds, mutatis mutandis, for neighboring pairs of scan lines.

FIG. 6 is a diagram illustrating the steps of a method (according to the present invention) for producing an electrical conductor. In step 601, an electrically conducting first layer, a laser beam, and a removal means is provided. In step 602, the laser beam is operated to ablate the first layer. The ablation produces a first set of depressions in the first layer that comprises at least two longitudinal depressions. Furthermore, the ablation is performed over a time interval $T_1$, while the removal means is operated over the time interval $T_2$. The interval $T_1$ is not only shorter than the interval $T_2$, but also fall completely within the interval $T_2$. After the ablation has been completed, the first layer is coated with an electrically conducting polymer in step 605.

FIG. 6 also shows that after the first set of depressions have been ablated, a further set of depressions can optionally also be ablated using the laser beam (step 603). Here the ablation is performed over a time interval $T_3$, while the removal means is operated over the time interval $T_4$. The interval $T_3$ is not only shorter than the interval $T_4$, but also fall completely within the interval $T_4$. Optionally, a depth of the longitudinal depressions in the first set of depressions can also be increased, as shown in step 604. Here the ablation is performed over a time interval $T_5$, while the removal means is operated over the time interval $T_6$. The interval $T_5$ is not only shorter than the interval $T_6$, but also fall completely within the interval $T_6$.

FIGS. 7 and 8 show experimental results of the impedance and charge storage capacity of an electrical conductor according to the invention, when the electrical conductor is subjected to an accelerated aging test (FIG. 7) and cyclic voltammetry stimulations (FIG. 8). The measurements of electrical conductors not according to the invention are shown for comparison. FIGS. 7 and 8 are discussed in more detail in the "Example" section below.

FIG. 9 shows photographs of the electrical conductor after the electrical conductor was subjected to cyclic voltammetry stimulations. FIG. 9 are discussed in more detail in the "Example" section below.

Figure 10:
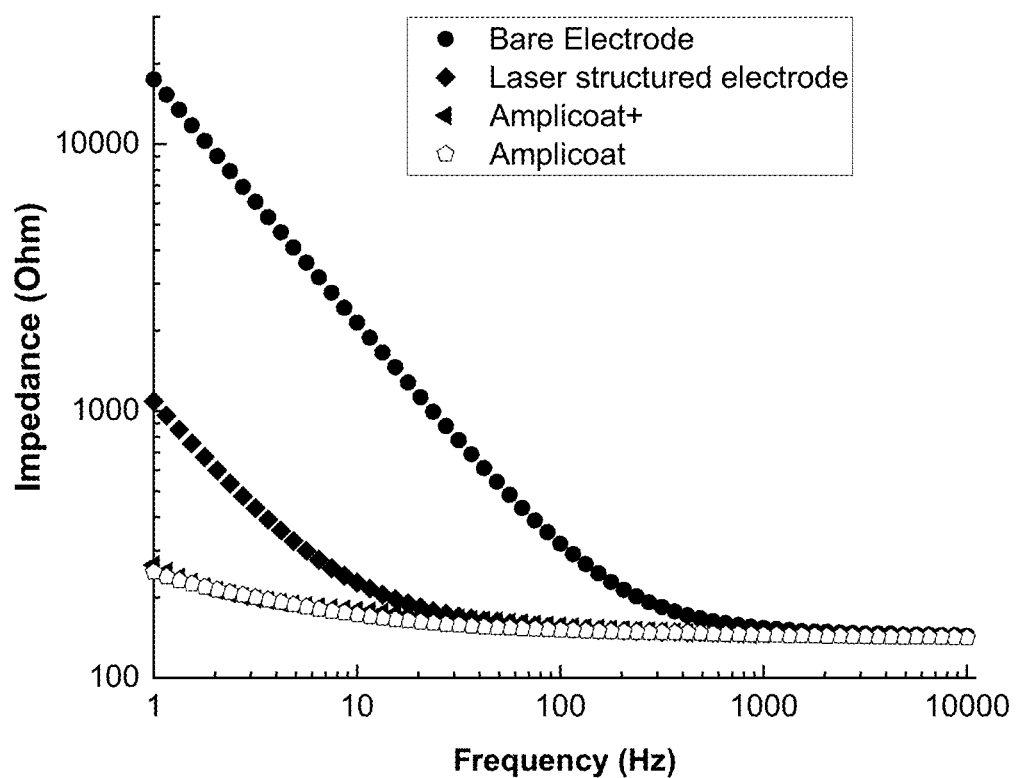
FIG. 10 is a graph illustrating electrical impedance as a function of frequency for various electrical conductors.

FIG. 10 shows the electrical impedance as a function of frequency for various electrical conductors. The measurements are explained in more detail in the "Example" section below.

EXAMPLES

The invention is now illustrated further by way of examples. The invention is not limited by the examples.

The following applies to comparative examples 1 to 3, as well as inventive examples 1 to 3. An electrical conductor with a first layer was provided. The first layer is in the form of a hollow cylinder. The thickness of the wall of the hollow cylinder, i.e., the first layer, is 102 μm, while the diameter of the cylindrical volume enclosed by the hollow cylinder is 1.3 mm. The first layer comprises platinum iridium (Pt/Ir 10). The direction along the length of the cylinder is defined as the axial direction. The direction along the circumference of the cylinder is defined as the tangential direction.

The following applies to comparative example 2 and inventive examples 1 to 3. The first layer was coated with a 10 μm layer of Amplicoat®. This coating is obtainable from Heraeus Deutschland GmbH & Co. KG (Germany). For inventive examples 1 to 3, the coating layer was applied after the laser ablation of the first layer was completed.

The following applies to comparative example 3 and inventive examples 1 to 3. The first layer was laser ablated. A first set of depressions was ablated along the axial direction of the first layer, while a further set of depressions was ablated along the tangential direction of the first layer. The longitudinal depressions in the first set of depressions were parallel to each other. The longitudinal depressions in the further set of depressions were parallel to each other, while also being perpendicular to the longitudinal depressions in the first set of depressions. The laser ablation of the longitudinal depressions led to the formation of macro protrusions. The widths of the longitudinal depressions in the first of depressions are measured along the tangential direction, while the widths of the longitudinal depressions in the further of depressions are measured along the axial direction.

The following also applies to comparative example 3 and inventive examples 1 to 3. For the ablation, an ultrashort pulsed laser beam, specified by a wavelength of 1030 nm, a pulse repetition rate of 200 kHz, and a pulse duration of 900 fs was used. The focal spot of the laser beam had a diameter of 20 μm. When scanning the laser beam in the axial direction, the energy of the laser beam was 0.74 W, while the energy of the laser beam, when scanning in the tangential direction, was 0.38 W. The scanning velocity was 150 mm/s in the axial direction, and 25 mm/s in tangential direction.

The following applies to comparative example 3 and inventive examples 1 to 3. During the laser ablation used to produce the longitudinal depression in the first set of depressions, as well as the longitudinal depression in the further set of depressions, a removal means was used. The removal means was an AD 1000 iQ, which is commercially available from BOFA International Ltd (UK). Additional details for each of the respective example are given below and in Table 1.

Comparative Example 1

The first layer was not laser ablated, i.e., the first layer did not have any depressions or macro protrusions. Furthermore, the electrical conductor did not have a coating layer.

Comparative Example 2

This example is similar to comparative example 1, with the exception that the first layer is coated with the Amplicoat® layer.

Comparative Example 3

Regarding the longitudinal depression in the first set of depressions: each longitudinal depression in the first set of depressions was produced by a single scan of the laser beam along the axial direction. Regarding the longitudinal depression in the further set of depressions: each longitudinal depression in the further set of depressions was produced by a single scan of the laser beam along the tangential direction. The distance between scan lines, in both the axial and tangential direction, was 20 μm.

Inventive Example 1

The longitudinal depression in the first set of depressions, as well as the longitudinal depressions in the further set of depressions, was produced in the same manner as comparative example 3. However, compared to comparative example 3, the first layer in inventive example 1 is coated with the Amplicoat® layer.

Inventive Example 2

Regarding the longitudinal depression in the first set of depressions: each longitudinal depression in the first set of depressions was produced by two scans of the laser beam along the axial direction, i.e., each depression was produced using a pair of scan lines. The width of the scan lines forming the pair of scan lines was 5 μm. The distance between neighboring pairs of scan lines was 20 μm. The ablation of the longitudinal depressions in the further set was performed in the same manner as inventive example 1.

Inventive Example 3

Regarding the longitudinal depression in the first set of depressions: each longitudinal depression in the first set of depressions was produced by three scans of the laser beam along the axial direction, i.e., each depression was produced using a triplet of scan lines. The width of the scan lines forming the triplet of scan lines was 5 μm. The distance between neighboring triplets of scan lines was 20 μm.

Regarding the longitudinal depression in the further set of depressions: each longitudinal depression in the further set of depressions was produced by two scans of the laser beam along the tangential direction, i.e., each depression was produced using a pair of scan lines. The width of the scan lines forming the pair of scan lines was 5 μm. The distance between neighboring pairs of scan lines was 20 μm.

Table 1 gives the values for a number of geometric properties that were measured for the first layer of the different examples. The values in Table 1 were measured after the ablation was completed, but prior to the coating of the first layer with the coating layer. Table 2 gives the values measured for various parameters of the electrical conductor after coating the first layer with the coating layer. Note that the values in Table 2 for comparative example 1 are measured for the first layer as the electrical conductor in comparative example 1 has no coating layer.

TABLE 1

| | values measured for first layer prior to coating | | | | |
|---|---|---|---|---|---|
| | Comparative 1 | Comparative 2 | Inventive 1 | Inventive 2 | Inventive 3 |
| First layer laser ablated | No | No | Yes | Yes | Yes |
| Conductor has coating layer | No | Yes | Yes | Yes | Yes |
| Laser exhaust used | — | — | Yes | Yes | Yes |
| Distance between scan lines (μm) | | | | | |
| axial | — | — | 20 | 20 | 20 |
| tangential | — | — | 20 | 20 | 20 |
| Depth: longitudinal depressions (μm) | — | — | At least 95% in range | At least 95% in range | At least 95% in range |
| first set | — | — | 9.9 to 11.3 | 9.8 to 11.3 | 13.4 to 14.8 |
| further set | — | — | 4.8 to 6.2 | 4.7 to 6.4 | 10.5 to 11.6 |
| Width: longitudinal depressions (μm) | — | — | At least 95% in range | At least 95% in range | At least 95% in range |
| first set | — | — | 12.5 to 14.3 | 12.2 to 14.1 | 13.6 to 16.2 |
| further set | — | — | 9.3 to 10.9 | 9.5 to 11.2 | 12.3 to 13.9 |
| Width: macro protrusions (μm) | — | — | At least 95% in range | At least 95% in range | At least 95% in range |
| axial | — | — | 9.1 to 10.7 | 8.8 to 10.5 | 6.1 to 7.7 |
| tangential | — | — | 5.7 to 7.5 | 5.9 to 7.8 | 3.8 to 6.4 |
| Width: micro protrusions (μm) | — | — | At least 50% in range | At least 90% in range | At least 90% in range |
| axial | — | — | 1.0 to 2.0 | <0.4 | <0.4 |
| tangential | — | — | 1.0 to 2.0 | <0.4 | <0.4 |
| Surface index | 1 | 1 | 2.6 | 3.4 | 4.2 |

TABLE 2

| | values measured for the conductor | | | | |
|---|---|---|---|---|---|
| | Comparative 1 | Comparative 2 | Inventive 1 | Inventive 2 | Inventive 3 |
| Charge storage capacity (mC/cm$^2$) | | | | | |
| ST | NA | NA | −26.93 +/− 2.75 | −26.98 +/− 4.69 | −20.76 +/− 1.8 |
| CVS | −1.7 | −14 | −16.3 +/− 1.68 (3000 cycles) | −12.74 +/− 1.74 (19000 cycles) | −13.673 +/− 0.172 (22000 cycles) |
| AAT (5 yrs) | −1.6 | −16.3 | −12.59 +/− 1.25 | −11.99 +/− 0.788 | NM |
| AAT (ST) (5 yrs) | NA | NA | −8.3 +/− 0.59 (5 yrs) | −11.298 +/− 0.324 (5 yrs) | NM |
| Impedance (Ω) | | | | | |
| ST | NA | NM | 185.363 +/− 25.69 | 162.76 +/− 20.26 | 126.75 +/− 13.93 |
| CVS | 18000 | 1000 | 152 +/− 12.36 (3000 cycles) | 284 +/− 53.97 (19000 cycles) | 404 +/− 7.02 (22000 cycles) |
| AAT (5 yrs) | 19000 | 1100 | 307 +/− 50 | 436 +/− 107 | NM |
| AAT (ST) (5 yrs) | NM | NM | 712 +/− 102 (5 yrs) | 691 +/− 20 (5 yrs) | NM |

TABLE 2-continued values measured for the conductor

| | Comparative 1 | Comparative 2 | Inventive 1 | Inventive 2 | Inventive 3 |
|---|---|---|---|---|---|
| Visible damage | | | | | |
| CVS | No change | after 1000 cycles: appearance of cracks in first layer, sections of coating layer dislodged from conductor | after 3000 cycles: appearance of cracks in first layer, sections of coating layer dislodged from conductor | after 12000 cycles: appearance of small cracks in first layer, appearance of small blisters in coating layer | after 22000 cycles: no visible damage to first layer or coating layer |
| Cleaning required | ---- | ---- | +++ | +++ | +++ |
| Signal to noise ratio | ---- | ++++ | ++++ | ++++ | ++++ |
| Long term Stability of electrical signal | +++ | + | ++ | +++ | ++++ |
| Adhesion of coating layer | NA | --- | + | ++ | +++ |

In table 2 above, "CVS" is cyclic voltammetry stimulation, "AAT" is an accelerated aging test, and "ST" is a swipe test. For the AAT, the value given in years below the measurement represent the estimated age of the electrical conductor when used under normal operating circumstances. These tests are discussed in more detail in the "Measurements" section below. An AAT with the further description "(ST)" indicates that the measurement was taken after performing a swipe test with a weight of 80 g. In this case, the AAT was first performed, followed by the swipe test, followed by the taking of the measurement. A value of "NM" indicates a value that is not measured, while a value "NA" indicates "not applicable".

For Table 2, the following parameters were measured. With the exception of comparative example 1, the conductor has both a first layer and a coating layer. A "+" indicates an improvement in the desired effect, while a "-" indicates a reduction in the desired effect:

Charge storage capacity: the charge storage capacity of the electrical conductor.

Impedance: the impedance of the electrical conductor.

Visible damage: damage such as cracks in the first layer, blister in the coating layer, or sections of the coating layer that have peeled off.

Cleaning required: the amount of cleaning the first layer requires during the production of the electrical conductor. A surface of the first layer very often has contaminants. These contaminants include organic and inorganic contaminants, e.g., carbon, potassium, silicon, calcium, sulphur, and aluminium. These contaminants have to be removed prior to coating the first layer with the coating layer, as these contaminants negatively affect the adhesion of the coating layer to the first layer.

Stability of electrical signal: The long-term variation in the electrical properties, e.g., the impedance and charge storage capacity, of the electrical conductor.

Adhesion of coating layer: how well the coating layer of the electrical conductor adheres to the first layer. If a section of the coating layer should become dislodged while the electrical conductor is inserted in a patient, this will lead to a problem for the patient. Good adhesion is also important for the electrical conductor to withstand mechanical forces and stresses. Such force can result from, e.g., inserting or withdrawing the electrical conductor from the body of a mammal, or by an operator handling the electrical conductor.

Figure 7A:
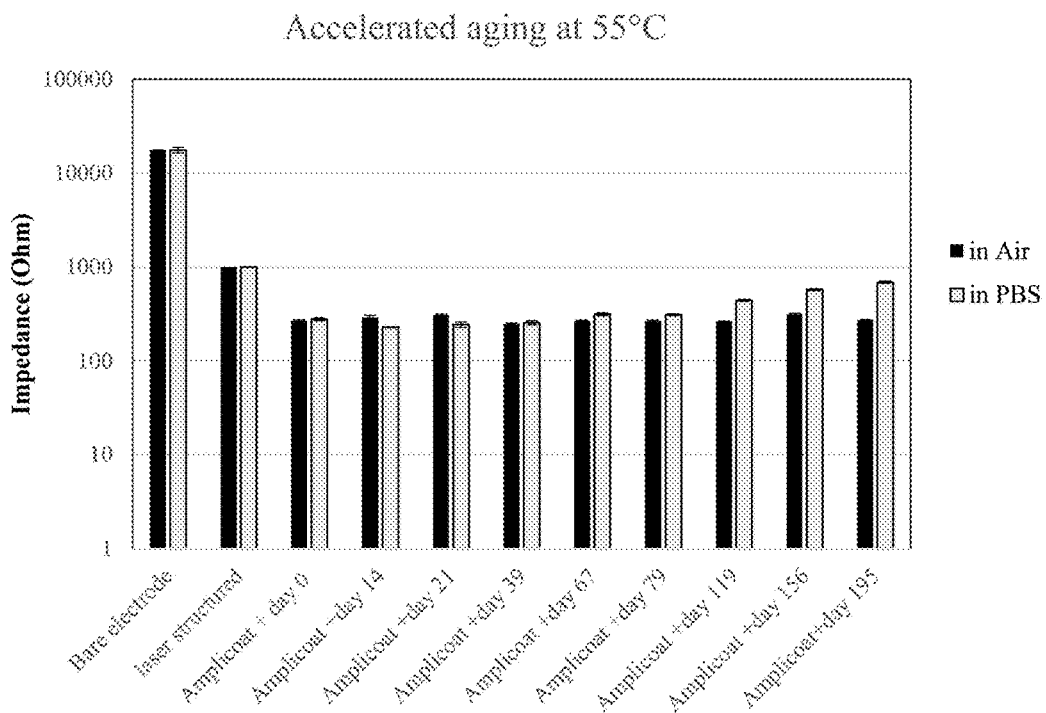
FIGS. 7A and 7B illustrate experimental results showing the impedance and charge storage capacity of an electrical conductor according to the invention, when the electrical conductor is subjected to an accelerated aging test.
Figure 7B:
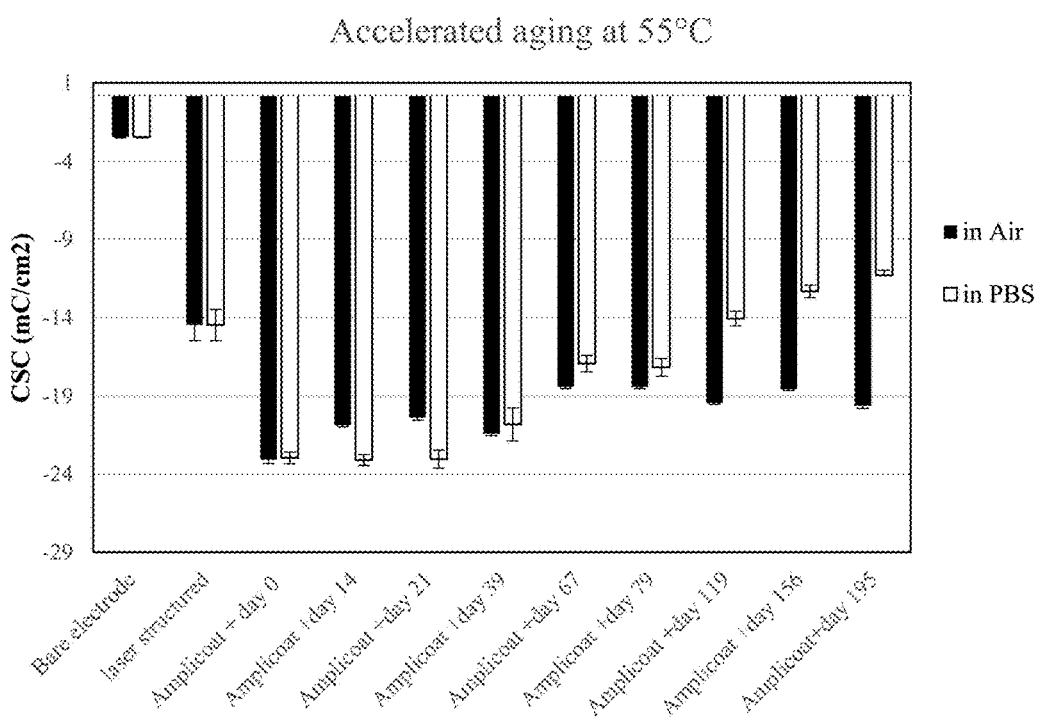

FIG. 7 shows graphs of the experimental results when the electrical conductor is subjected to an accelerated aging test (AAT). Each bar represents an average measurement taken over 12 electrical conductors. FIG. 7 further shows that the AAT was performed in both air and a phosphate-buffered saline solution (PBS). FIG. 7A shows the impedance (measured at 1 Hz) of the electrical conductor as a function of time, while FIG. 7B shows the measured charge storage capacity (CSC) of the electrical conductor as a function of time. In FIG. 7, day=195 of the AAT is equivalent to approximately 5 years under normal operating circumstances. The first set of bars ("Bare electrode") in FIG. 7 are the impedance and CSC of an electrical conductor according to comparative example 1, measured at day=0. The second set of bars in FIG. 7 ("Laser structured") are the impedance and CSC of an electrical conductor according to comparative example 3, measured at day=0. The remaining bars in FIG. 7 ("Amplicoat+") are the impedance and CSC of an electrical conductor according to inventive example 2, measured at different days. FIG. 7A shows that inventive example 2 provides an improvement over comparative examples 1 and 3, i.e., a lower impedance. While the impedance of inventive example 2 increases with time, the impedance is still lower than comparative examples 1 and 3 (which were both measured at day=0). Furthermore, inventive example 2 provides very good long-term stability of the impedance. FIG. 7B shows that inventive example 2 provides an improvement over comparative examples 1 and 3, i.e., an increased CSC. While the CSC of inventive example 2 decreases with time, the CSC is still better than comparative examples 1 and 3 (which were both measured at day=0) up to day=79. Furthermore, inventive example 2 provides good long-term stability of the CSC.

Figure 8A:
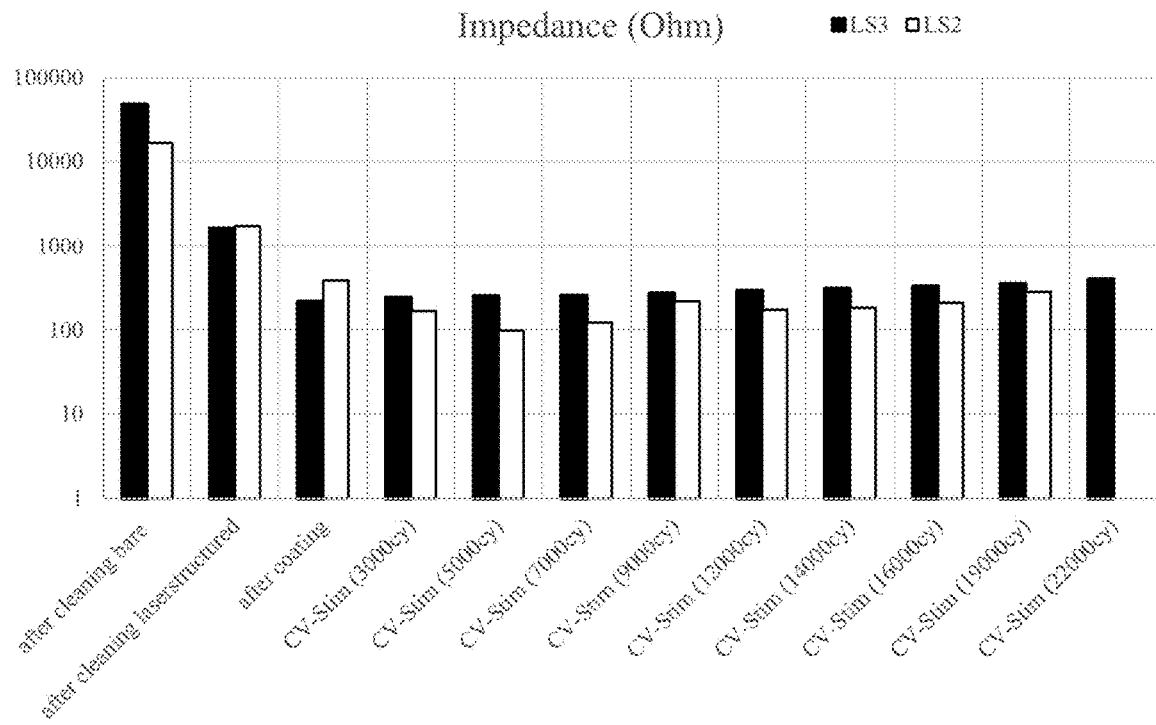
FIGS. 8A and 8B illustrate experimental results showing the impedance and charge storage capacity of an electrical conductor according to the invention, when the electrical conductor is subjected to cyclic voltammetry stimulations.
Figure 8B:
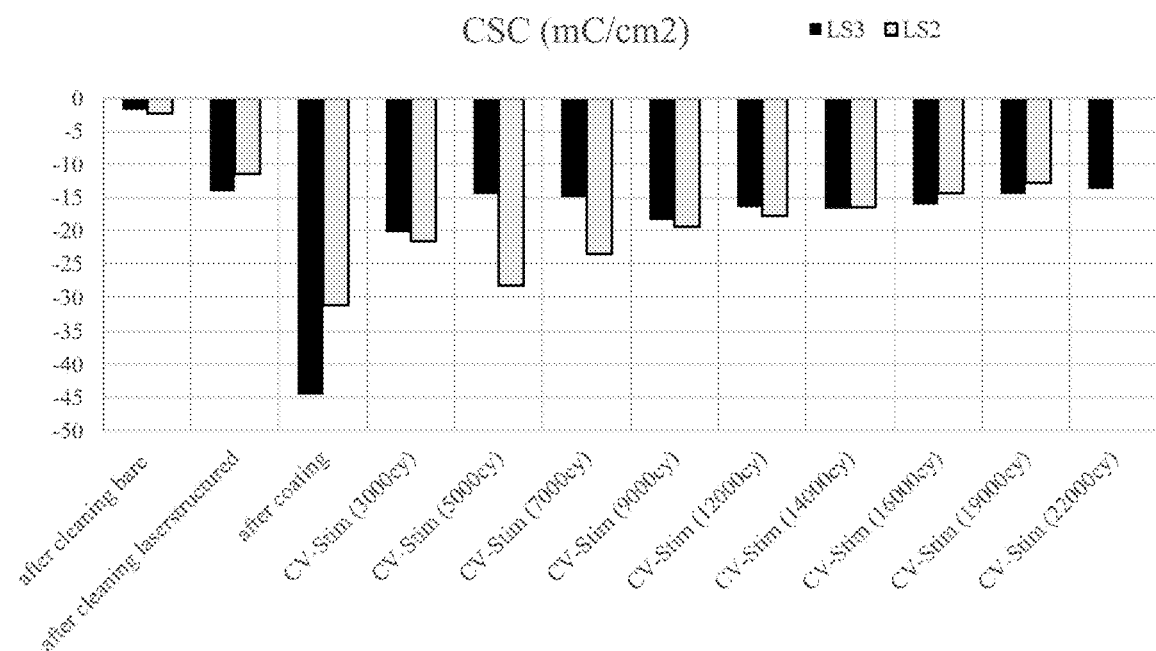
Figure 9A:
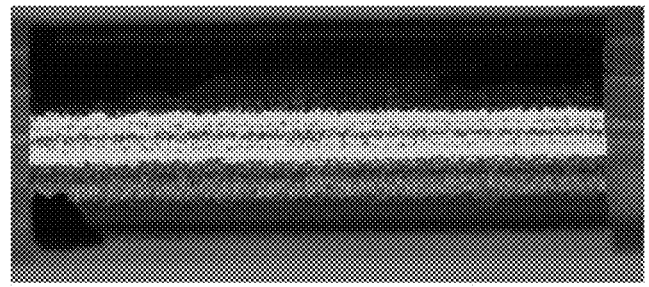
FIGS. 9A to 9D are photographs of an electrical conductor after being subjected to cyclic voltammetry stimulations.
Figure 9B:
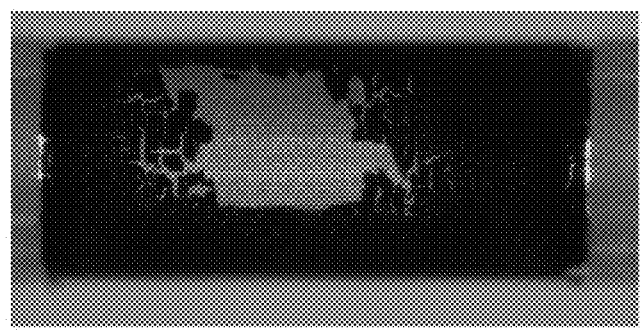
Figure 9C:
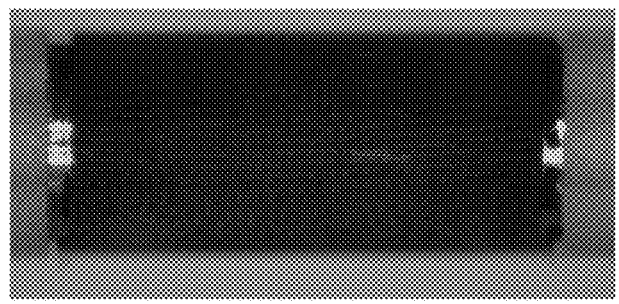
Figure 9D:
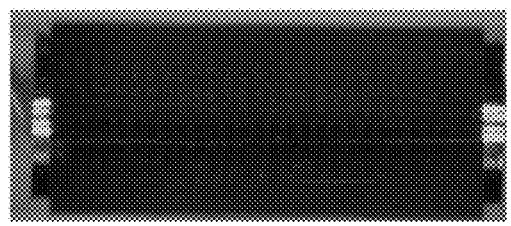

FIG. 8 shows graphs of the experimental results when the electrical conductor is subjected to cyclic voltammetry stimulations (CVS). Each bar represents an average measurement taken over 12 electrical conductors. For FIG. 8, the CVS was performed in a phosphate-buffered saline solution (PBS). FIG. 8A shows the impedance (measured at 1 Hz) of the electrical conductor as a function of the number of CV cycles, while FIG. 8B shows the measured charge storage capacity (CSC) of the electrical conductor as a function of the number of CV cycles. The white bars ("LS2") represent the measurements for inventive example 2, while the black bars ("LS3") represent the measurements for inventive example 3. The first set of bars in FIG. 8 ("after cleaning bare") are the impedance and CSC of the first layer after cleaning contaminants from the surface of the first layer, but prior to the laser structuring of the first layer. The second set of bars in FIG. 8 ("after cleaning laser structured") are the impedance and CSC of the electrical conductor measured prior to coating the first layer with the Amplicoat, i.e., the measurements are for first layer. The third set of bars in FIG. 8 ("after coating") are the impedance and CSC of the electrical conductor after the first layer is coated with the Amplicoat, but prior to performing any CVS. FIG. 8A shows that inventive examples 2 and 3 provides an improvement, i.e., a lower impedance, over an uncoated electrical conductor that has not been laser ablated, as well as an uncoated electrical conductor that has been laser ablated. This improvement is seen even after the electrical conductor of inventive examples 2 and 3 have been subjected to CVS. Furthermore, inventive examples 2 and 3 provide very good long-term stability of the impedance. FIG. 8B shows that inventive examples 2 and 3 provides a significant improvement, i.e., an increased CSC, over an uncoated electrical conductor that has not been laser ablated, as well as an uncoated electrical conductor that has been laser ablated. While the CSC decreases for inventive examples 2 and 3 after being subjected to CVS, the CSC is still better than the uncoated electrical conductor. It should also be kept in mind that the first three sets of bars are the measurements prior to any CVS, and that a decrease in CSC is expected when CVS is performed on an electrical conductor. Furthermore, inventive examples 2 and 3 provide good long-term stability of the CSC.

FIG. 9 shows photographs of the electrical conductor after the electrical conductor was subjected to CVS. FIG. 9A shows the electrical conductor according to comparative example 2, after having being subjected to 1000 CV cycles. It can be seen that the coating layer (dark section) has almost completely detached from the first layer (light section). FIG. 9B shows the electrical conductor according to inventive example 1, after having being subjected to 3000 CV cycles. It can be seen that parts of the coating layer (dark section) have become detached from the first layer (light section). FIG. 9C shows the electrical conductor according to inventive example 2, after having being subjected to 10 000 CV cycles. It can be seen that the coating layer (dark section) is still attached to the first layer. FIG. 9D shows the electrical conductor according to inventive example 3, after having being subjected to 19 000 CV cycles. It can be seen that the coating layer (dark section) is still attached to the first layer. Inventive examples 1 to 3 are thus a significant improvement over comparative example 2. Furthermore, inventive examples 2 and 3 are a significant improvement over inventive example 1.

FIG. 10 show the electrical impedance as a function of frequency. The "Bare Electrode" is an electrical conductor according to comparative example 1. The "Amplicoat" is an electrical conductor according to comparative example 2. The "Laser structured electrode" is an electrical conductor according to comparative example 3. The "Amplicoat+" is an electrical conductor according to inventive example 2. It can be seen that the coating layer ("Amplicoat" and "Amplicoat+") provides a significant improvement in the impendence of the electrical conductor. However, as shown in Table 2, comparative example 2 ("Amplicoat") has very poor adhesion properties compared to inventive example 2 ("Amplicoat+").

Measuring Methods

The test methods which follow were utilized within the context of the invention. Unless stated otherwise, the measurements were conducted at an ambient temperature of 23° C., an ambient air pressure of 100 kPa (0.986 atm), and a relative air humidity of 50%.

Dimensions of Protrusions and Longitudinal Depressions

The dimensions of the macro protrusions, the micro protrusions, and longitudinal depressions, along a specific direction, is measured using a laser scanning microscope and 3D profilometry. A VK-X210 laser scanning microscope obtained from Keyence (Japan) was used.

The dimensions of the macro protrusions, the micro protrusions, and longitudinal depressions, along a specific direction, is measured as follows. 10 cross-sectional scans are made of the electrical conductor along the specific direction (e.g., FIG. 4A). Furthermore, the 10 cross-sectional scans are made at 10 different, evenly spaced positions on the electrical conductor.

Using the procedure explained in FIGS. 4B and 4C, the widths of the macro protrusions and micro protrusions, as well as the widths and depths of the longitudinal depressions are calculated. For multiple cross-sectional scans, each of the cross-sectional scans are arranged on the same graph, e.g., an y-z graph, such that the lowest point, $M_{min}$, of each cross-sectional scan touches the same axis. The average height of the macro protrusions, $H_{avg}$, is calculated using the heights of all of the macro protrusions in the 10 cross-sectional scans. The intermediate height value, h, is then calculated as $$h=0.85*H_{avg}.$$

Thickness of the Layers

The same 10 cross-sectional scans, used to measure the widths of the macro protrusions and the micro protrusions along a specific direction, is also used to measure the thickness of the first layer. The thickness of the first layer is defined as the average height $H_{avg}$ of the macro protrusions. The thickness of the at least one coating layer is calculated by subtracting the thickness of the first layer from the total thickness of the electrical conductor.

Water Contact Angle and Surface Energy

The water contact angle and surface energy are measured using an OCA 50 measuring device obtainable from Dataphysics Instruments GmbH (Germany). The measurement is performed according to the standard ASTM D7490-13.

Distance Between Scan Lines

The distance between the scan lines, neighboring pairs of scan lines, and neighboring triplets of scan lines, as well as the width of a pair of scan lines, and a width of a triplet of scan lines, is measured as explained in FIG. 5. The distance between scan lines, as well as any other dimension in the nano- or micrometer range, as described herein, can be determined by the skilled person using scanning electron microscopy (SEM).

Spectrum and Peak Wavelength

In case of a laser beam as beam of electromagnetic radiation, the peak wavelength of the spectrum is the nominal peak wavelength of the laser output. This is either the wavelength at which the laser, which produces the laser beam, lases or, if a non-linear optical process is used to alter the output wavelength, the respective harmonic of the lasing wavelength. For example, a KrF-Excimer laser typically has a lasing wavelength at about 248 nm. A Nd:YVO4-laser typically has a lasing wavelength at about 1064 nm. If the light of the Nd:YVO4-laser is frequency doubled, the peak wavelength of the laser output is at about 532 nm. If the beam of electromagnetic radiation is not a laser beam, the spectrum of this electromagnetic radiation is measured using a spectrometer of the type CCS200 from Thorlabs GmbH. The measurement is conducted in accordance with the manufacturer's instructions. The peak wavelength of the measured spectrum is then a local maximum of the spectrum which is also its global maximum.

Pulse Frequency

The pulse frequency is defined as the number of pulses, emitted per unit of time. The pulse frequency of a pulsed laser beam is adjusted at the laser producing the laser beam. Any pulse frequency, referred to herein, means the pulse frequency as adjusted at the laser producing the laser beam.

Pulse Duration

The pulse duration is defined as the time duration between the intensity levels of a pulse measured at FWHM (full width at half-maximum). It is measured with a suitable photo diode and an oscilloscope.

Fluence

The fluence is defined as energy per pulse [J]/effective focal spot area [$cm^2$]. Therein, the effective focal spot area is calculated as the area of a circle of a diameter which is the spot size according to the test method below.

Energy Per Pulse

The energy per pulse is determined by first measuring the accumulated energy of the laser beam over a period of irradiation of 1 second using a thermal power meter. If the focus of the laser beam is on the workpiece, this energy is measured right in front of the workpiece, i.e., slightly out of the focus point. The pulse frequency is determined as described above. The energy per pulse is calculated by dividing the accumulated energy by the pulse frequency in Hz.

Spot Size

The 2D-intensity distribution of the spot is measured using a 2D power meter. The spot size is determined by fitting a circle to the Full Width at Half Maximum of the 2D-intensity distribution. The spot size is the diameter of this circle.

Weight Percentage

This is determined by quantitative analytical methods. E.g., gas chromatography, gravimetry, elementary analysis or the like.

Electrical Impedance

For determining electrical impedance, electrochemical impedance spectroscopy was used. The electrical impedance was measured using a VMP3 potentiostat, obtainable from BioLogic (France). The measurement range was from 1 Hz to 10,000 Hz, and the sinus wave amplitude was 5 mV.

Charge Storage Capacity

For determining charge storage capacity (CSC), a VMP3 potentiostat, obtainable from BioLogic (France), was used. For the CSC, two cycles of cyclic voltammetry (CV) scans were performed in a phosphate-buffered saline solution (PBS) at a potential range from −0.6 V to +0.8 V and a speed of 100 mV/s. Furthermore, the PBS is at 23° C. and has a pH=7.4. A three-electrode configuration with an Ag/AgCl reference electrode was used for the measurements.

Surface Index

The surface index is the ratio of the geometrical surface area to the nominal surface area. The nominal surface area is the surface area of the first layer prior to laser ablation. The geometrical surface area is the surface area of the first layer after laser ablation. A VK-X210 laser scanning microscope obtained from Keyence (Japan) was used. This microscope includes software which was used to calculate the surface index.

Accelerated Aging Test

Two variations of the accelerated aging test (AAT) are performed. In the first variation, the electrical conductor is submerged in a phosphate-buffered saline solution (PBS), where the PBS is at 55° C. and has a pH=7.4. In the second variation, the electrical conductor is left in air that has a temperature of 55° C. In both variations, of the AAT is performed for 195 days, with the impedance and CSC measured at the days as shown in FIG. 7. For the PBS variation, 195 days in the AAT is equivalent to keeping the electrical conductor for 5 years in vivo at a temperature of 37° C.

Cyclic Voltammetry Stimulation

In this test, a VMP3 potentiostat, obtainable from BioLogic (France), was used. The electrical conductor is exposed to a number of cycles of cyclic voltammetry (CV) scans (see FIG. 8), which were performed in a phosphate-buffered saline solution (PBS) at a potential range from −0.6 V to +0.8 V and a speed of 100 mV/s. Furthermore, the PBS is at 23° C. and has a pH=7.4.

Adhesion of the Coating Layer and Swipe Test

The adhesion of the coating layer is tested using a swipe test. The procedure of the swipe test is as follows: all materials, devices, and surfaces that are to come into contact with the electrical conductor is first cleaned with 70% ethanol and a lint free cloth, and allowed to dry in air. The electrical conductor is then submerged in a first phosphate-buffered saline solution (PBS) for 15 minutes, where the PBS is at 23° C. and has a pH=7.4. The electrical conductor is then removed from the PBS, and a polyurethane (PU) foam, with a thickness of 2.5 mm, is then submerged in a second PBS, also for 15 minutes. The electrical conductor is then fixed to a work surface using adhesive tape (Scotch® Magic Tape, obtainable from 3M, USA), while the PU foam is attached to a mounting that is adapted and arranged to hold the PU foam. The electrical conductor is then covered with the PBS using a Pasteur pipette. The mounting with the PU foam is then lowered and the PU foam is brought into contact with an end of the electrical conductor, so that the PU foam exerts a weight on the electrical conductor. The PU foam is then moved 10 times along the length of the electrical conductor.

For testing the adhesion of the coating layer, a starting weight of 40 g is used. The weight is then increased in increments of 5 g up to a weight of 80 g. After each incremental increase in weight, the PU foam is moved 10 times along the length of the electrical conductor.

REFERENCE LIST

100 Electrical conductor
101 First layer
102 Micro protrusion
103 Macro protrusion
104 Longitudinal depressions in first set of depressions
105 Longitudinal depressions in further set of depressions
106 Coating layer
200 Images of first layer 201 First layer
203 Macro protrusion
204 Longitudinal depressions in first set of depressions
205 Longitudinal depressions in further set of depressions
300 Images of first layer
301 First layer
302 Micro protrusion
303 Macro protrusion
304 Longitudinal depressions in first set of depressions
305 Longitudinal depressions in further set of depressions
400 Cross-sectional scan of first layer
401 First layer
402 Micro protrusion
403 Macro protrusion
404 Longitudinal depressions in first set of depressions
500 Distance between scan lines
501 First layer
510 First triplet of scan lines
511 Further triplet of scan lines
512 Width of scan lines in first triplet of scan lines
513 Width of scan lines in further triplet of scan lines
514 Distance between neighboring triplets of scan lines
600 Method for producing electrical conductor
601 Provide first layer, laser beam, removal means
602 Operate laser beam to ablate first set of depressions in first layer
603 Operate laser beam to ablate further set of depressions in first layer
604 Increase depth of first set of depressions using laser beam
605 Coat first layer with coating layer

The invention claimed is:

1. An electrical conductor comprising
    a. a first layer, wherein the first layer
        i. is electrically conducting, and
        ii. comprises
            A. micro protrusions,
            B. macro protrusions, wherein the micro protrusions are arranged on the macro protrusions,
            C. a first set of depressions, wherein the first set of depressions comprises at least two longitudinal depressions;
            D. the macro protrusions and the at least two longitudinal depressions are arranged in an alternating pattern,
    b. at least one coating layer, wherein the at least one coating layer
        i. comprises an electrically conducting polymer,
        ii. touches the first layer,
        iii. at least partially covers the first layer;
    wherein
        I. at least 50% of the macro protrusions have a width, measured along a first direction, in the range of 2.0 µm to 40.0 µm;
        II. at least 50% of the micro protrusions have a width, measured along the first direction, in the range of 0.001 µm to 1.000 µm.

2. The electrical conductor according to claim 1, wherein the first layer further comprises a further set of depressions, wherein the further set of depressions comprises at least two longitudinal depressions.

3. The electrical conductor according to claim 2, wherein at least one of the following applies:
    a. at least 50% of the macro protrusions have a width, measured along a further direction, in the range of 2.0 µm to 40.0 µm;
    b. at least 50% of the micro protrusions have a width, measured along the further direction, in the range of 0.001 µm to 1.000 µm.

4. The electrical conductor according to claim 1, wherein at least one of the following applies:
    a. at least 50% of the longitudinal depressions in the first set of depressions have a ratio of a depth to a width that is in the range of 0.01 to 3.00; and
    b. at least 50% of the longitudinal depressions in the further set of depressions have a ratio of a depth to a width that is in the range of 0.01 to 2.00.

5. The electrical conductor according to claim 1, wherein at least one of the following applies:
    a. at least 50% of the longitudinal depressions in the first set of depressions are parallel to each other;
    b. at least 50% of the longitudinal depressions in the further set of depressions are parallel to each other; and
    c. at least 50% of the longitudinal depressions in the first set of depressions are perpendicular to at least 50% of the longitudinal depressions in the further set of depressions.

6. The electrical conductor according to claim 1, wherein at least one of the following applies:
    a. at least 50% of the longitudinal depressions in the first set of depressions have a depth that is in the range of 5.0 µm to 30.0 µm; and
    b. at least 50% of the longitudinal depressions in the further set of depressions have a depth in the range of 1.0 µm to 18.0 µm.

7. The electrical conductor according to claim 1, wherein at least one of the following applies:
    a. at least 50% of the longitudinal depressions in the first set of depressions have a width in the range of 1.0 µm to 200.0 µm; and
    b. at least 50% of the longitudinal depressions in the further set of depressions have a width in the range of 1.0 µm to 200.0 µm.

8. The electrical conductor according to claim 1, wherein the electrically conducting polymer comprises
    a. poly(3,4-ethylenedioxythiophene) (PEDOT), a functionalized derivative of PEDOT, or a mixture thereof;
    b. at least one photoreactive component comprising an anionic photoreactive hydrophilic polymer; and
    c. at least one of the following: a polyacetylene, a poly (fluorene), a polyphenylene, a polyphenylene vinylene, a polypyrene, a polyazulene, a polynaphthalene, a poly(pyrrole), a polycarbazole, a polyindole, a polyazepine, a polyaniline, a polyacene, a polythiophene, a polythiophene vinylene, a poly(p-phenylene sulfide), a polypyridine, or functionalized derivatives, precursors or blends of two or more thereof.

9. The electrical conductor according to claim 1, wherein the first layer comprises a metal, a metal alloy, or a combination thereof.

10. A method for producing an electrical conductor, comprising the steps of
    a. providing
        i. a first layer, wherein the first layer is electrically conducting,
        ii. at least one laser beam,
        iii. a removal means;

b. operating the at least one laser beam to ablate the first layer, wherein the ablation
   i. produces a first set of depressions in the first layer, wherein the first set of depressions comprises at least two longitudinal depressions;
   ii. is performed over a time interval $T_1$;
c. coating the first layer with at least one coating layer, wherein the at least one coating layer comprises an electrically conducting polymer;
wherein
   the removal means is operated over a time interval $T_2$, and wherein the time intervals $T_1$ and $T_2$ at least partially overlap.

11. The method according to the preceding claim 10, wherein the removal means is selected from the group consisting of a laser exhaust and a laser dust removal system.

12. The method according to claim 10, further comprising the step of operating the at least one laser beam to ablate the first layer, wherein
   A. the ablation
      i. produces a further set of depressions in the first layer, wherein the further set of depressions comprises at least two longitudinal depressions,
      ii. is performed over a time interval $T_3$; and
   B. the removal means is operated over a time interval $T_4$, and wherein the time intervals $T_3$ and $T_4$ at least partially overlap.

13. The method according to claim 10, wherein the removal means has a volume flow rate in the range of 150 m³/h to 5000 m³/h.

14. The method according to claim 10, further comprising at least one of the following steps:
   a. increasing a depth of at least 50% of the longitudinal depressions in the first set of depressions by laser ablation; and
   b. increasing a depth of at least 50% of the longitudinal depressions in the further set of depressions by laser ablation.

15. The method according to claim 10, wherein at least one of the following applies:
   a. at least 50% of the longitudinal depressions in the first set are parallel to each other;
   b. at least 50% of the longitudinal depressions in the further set are parallel to each other; and
   c. at least 50% of the longitudinal depressions in the first set are perpendicular to at least 50% of the longitudinal depressions in the further set.

16. An electrical conductor obtainable according to the method of claim 10.

17. An electrode comprising at least one electrical conductor according to claim 10.

18. An electrical device comprising the electrode according to claim 17.

* * * * *